United States Patent
Sommazzi et al.

(10) Patent No.: US 9,290,586 B2
(45) Date of Patent: Mar. 22, 2016

(54) SOLID CATALYST COMPONENT, CATALYST COMPRISING SAID SOLID COMPONENT, AND PROCESS FOR THE (CO)POLYMERIZATION OF α-OLEFINS

(75) Inventors: Anna Sommazzi, Novara (IT); Francesco Masi, Sant'Angelo Lodigiano-Lodi (IT); Guido Pampaloni, Pontedera (IT); Filippo Renili, Pisa (IT); Fabio Marchetti, Pisa (IT); Anna Maria Raspolli Galletti, Titignano Pisa (IT)

(73) Assignee: Versalis S.P.A. (IT)

( * ) Notice: Subject to any disclaimer, the term of this patent is extended or adjusted under 35 U.S.C. 154(b) by 162 days.

(21) Appl. No.: 13/997,967

(22) PCT Filed: Dec. 20, 2011

(86) PCT No.: PCT/EP2011/073429
§ 371 (c)(1),
(2), (4) Date: Jul. 23, 2013

(87) PCT Pub. No.: WO2012/089562
PCT Pub. Date: Jul. 5, 2012

(65) Prior Publication Data
US 2013/0303360 A1   Nov. 14, 2013

(30) Foreign Application Priority Data

Dec. 27, 2010   (IT) .................. MI10A2401

(51) Int. Cl.
| | | |
|---|---|---|
| *C08F 10/02* | (2006.01) | |
| *C07F 17/00* | (2006.01) | |
| *C08F 4/659* | (2006.01) | |
| *C08F 110/02* | (2006.01) | |
| *C08F 210/16* | (2006.01) | |

(52) U.S. Cl.
CPC ............... *C08F 10/02* (2013.01); *C07F 17/00* (2013.01); *C08F 4/65912* (2013.01); *C08F 110/02* (2013.01); *C08F 210/16* (2013.01)

(58) Field of Classification Search
None
See application file for complete search history.

(56) References Cited

U.S. PATENT DOCUMENTS

| | | | | |
|---|---|---|---|---|
| 4,329,253 | A * | 5/1982 | Goodall et al. ............... | 502/111 |
| 5,631,334 | A * | 5/1997 | Zandona ...................... | 526/113 |
| 5,821,189 | A | 10/1998 | Calderazzo et al. | |

OTHER PUBLICATIONS

Calcalderazzo, Fausto, et al., "Arene Derivitives of Zirconium(II) and Hafnium(II)", Journal of the Chemical Society, Dalton Transactions, Chemical Society. Letchworth, GB, Jan. 1, 1990, pp. 1813-1818.

Troyanov, S., et al., "The Synthesis and Crystal Structure of n-mesitylenezirconium(II) bromine complexes [(n6-C6H3Me3)2Zr(u-Br)2AlBr2]. . . (Al2Br2] and [(n6-C6H3Me3)2Zr(u-Br)2 . . . AlBr2](Al20Br8)", Organometallic Chemistry in the USSR, Turpin Transactions LTD, Letchworth, GB, vol. 5, No. 5, Jan. 1, 1992.

Troyanov, S., et al., Synthesis of Arene Ti and Zr complexes and their reactivity towards air: crystal structure of [(C6H3Me3)2Zr(AlC14)](Al2C17) and TiCl3(0Ph). Journal of Organometallic Chemistry, Elsevier-Sequoia S.A. Lausanne, CH, vol. 494, No. 1, May 31, 1995.

\* cited by examiner

*Primary Examiner* — Yun Qian
(74) *Attorney, Agent, or Firm* — Tarolli, Sundheim, Covell & Tummino LLP

(57) ABSTRACT

A solid catalyst component for the (co)polymerization of α-olefins having general formula (I): $Zr_nMAl_xClMg_p$ (I) wherein: M represents titanium (Ti), vanadium (V), or mixtures thereof; n is a number ranging from 0.01 to 2; x is a number ranging from 0.1 to 4; y is a number ranging from 5 to 53; p is a number ranging from 0 to 15; obtained by means of a process comprising putting at least one zirconium arene in contact with at least one metal compound and, optionally, with at least one compound of magnesium. Said solid catalyst component can be advantageously used as a solid component in a catalyst for the (co)polymerization of α-olefins. Said catalyst can be advantageously used in a process for the (co)polymerization of α-olefins.

10 Claims, No Drawings

SOLID CATALYST COMPONENT, CATALYST COMPRISING SAID SOLID COMPONENT, AND PROCESS FOR THE (CO)POLYMERIZATION OF α-OLEFINS

RELATED APPLICATION

This application is a National Phase filing of PCT/EP2011/073429, filed Dec. 20, 2011, and claims priority to Italian Application No. MI2010A002401, filed Dec. 27, 2010, the subject matter of which are incorporated herein by reference in their entirety.

The present invention relates to a solid catalyst component for the (co)polymerization of α-olefins.

More specifically, the present invention relates to a solid catalyst component for the (co)polymerization of α-olefins obtained by means of a process comprising putting at least one zirconium arene in contact with at least one metal compound and, optionally, with at least one compound of magnesium.

The present invention also relates to a catalyst for the (co)polymerization of α-olefins comprising said solid component.

Furthermore, the present invention relates to a process for the (co)polymerization of α-olefins, characterized in that it uses said catalyst.

In addition, the present invention relates to a zirconium alkyl arene having general formula (III) or (IIIa) indicated hereunder, as well as the process for its preparation.

Solid components for catalysts for the (co)polymerization of α-olefins are described in the art.

For example, the U.S. Pat. No. 4,987,111 describes a solid catalyst component for the polymerization of ethylene and the copolymerization of ethylene with $C_3$-$C_{10}$ α-olefins, having formula $VTi_nCl_{4n}$ wherein n ranges from 1 to 3, said solid catalyst component being prepared by reacting titanium tetrachloride with a vanadium arene $[V^0(arene)_2]$ according to the following equation:

$$V^0(arene)_2 + nTiCl_4 \rightarrow VTi_nCl_{4n} + 2 arene$$

wherein said arene is selected from non-substituted benzene or benzene substituted with at least one $C_1$-$C_3$ alkyl group, and having a particle diameter ranging from 5 to 20 μm, said particles having a surface area ranging from 10 m²/g to 70 m²/g and an average pore diameter ranging from 10,000 Å to 20,000 Å.

U.S. Pat. No. 4,980,491 describes a process for the preparation of vanadium-arenes $[V(arene)_2]$, wherein "arene" means benzene or mono-, di- or polyalkyl-substituted benzene, through the reduction of a vanadium-arene iodide $[V(arene)_2I]$, characterized in that a compound selected from the group consisting of zinc, manganese or iron in metal form, or cobalt dicyclopentadienyl, is used as reducing agent.

Said vanadium-arenes are useful in the preparation of catalyst components active in the polymerization of ethylene or in the copolymerization of ethylene with α-olefins.

U.S. Pat. No. 5,093,508 describes a process for the preparation of vanadium-arenes $[V(arene)_2]$, wherein arene means benzene or mono-, di- or poly-alkyl $C_1$-$C_5$ substituted benzene, characterized in that:

(a) a complex $[V(arene)_2](+)AlCl_4(-)$ is obtained from the reaction of vanadium trichloride, metal aluminium and aluminium trichloride in the presence of the selected arene;

(b) the complex thus obtained is treated with a cyclic, acyclic or aliphatic ether to obtain the reduction of $[V(arene)_2](+)$ to $[V(arene)_2]$; and (c) the vanadium-arene thus obtained is recovered.

Said vanadium-arenes are useful in the preparation of catalysts active in the polymerization of olefins.

U.S. Pat. No. 5,210,244 describes a process for the preparation of a vanadium-bis arene $[V(arene)_2]$, starting from vanadium oxychloride, aluminium metal, aluminium trichloride and an arene, said process comprising:

(a) putting vanadium oxychloride ($VOCl_3$), aluminium metal and aluminium trichloride in contact in the liquid arene, in order to transform the vanadium oxychloride into the following reaction product: $[V(arene)_2](+)AlCl_4(-)$;

(b) adding a cyclic or acyclic liquid ether to the reaction product obtained in step (a) to reduce $[V(arene)_2](+)$ to $[V(arene)_2]$; and (c) recovering the vanadium bis-arene $[V(arene)_2]$ from the reaction product obtained in step (b).

Said vanadium bis-arene is useful in the preparation of catalysts active in the polymerization of olefins.

U.S. Pat. No. 5,821,189 describes a catalyst for the (co)polymerization of ethylene obtained by means of a process which comprises putting the following components (A), (B) and, optionally (C) and (D) in contact in the following molar ratios (A):(B):(C):(D)=(1):(0.5-2):(0-25):(0-15), said components being:

(A) a bivalent titanium-arene having formula $Ti(\eta^6\text{-arene})(AlR_xX_{4-x})_2$;

(B) a compound or a mixture of compounds selected from the group consisting of titanium, zirconium, vanadium, hafnium, tin, germanium, cerium and osmium halides, in oxidation state (+4) and of antimony or vanadium in oxidation state (+5); and derivatives of these metals in said oxidation state with oxygenated ligands, wherein at least one of the oxygen atoms of said ligands is bound to or coordinated with the metal;

(C) optionally, an organic compound of aluminium having formula $AlR'_zZ_{3-z}$;

(D) optionally, an organic chloro-derivative selected from the group consisting of:
  (a) di- and poly-chloroalkanes;
  (b) alkyl esters of aliphatic carboxylic acids, di- and trichloro-substituted in the carbon in alpha position with respect to the carboxyl; and
  (c) derivatives of chlorotriphenylmethane and dichlorodiphenylmethane having a carboxyalkyl group in para position in at least one of the phenyl rings;

wherein, in the above formulae:
  arene represents benzene or benzene substituted with from 1 to 6 $C_1$-$C_6$ alkyl groups;
  X represents a chlorine, bromine or fluorine atom;
  Z represents a chlorine or bromine atom;
  R represents a linear or branched $C_1$-$C_{10}$ alkyl group;
  R' represents a linear or branched $C_1$-$C_{10}$ alkyl group;
  x is a number varying from 1 to 2;
  z is a number varying from 1 to 3.

The Applicant has faced the problem of finding a solid catalyst component containing zirconium and another metal selected from titanium, vanadium or mixtures thereof, capable of providing a bimetal catalyst for the (co)polymerization of α-olefins.

The Applicant has now found that by putting at least one zirconium arene, with zirconium in a bivalent state, in contact with at least one metal compound wherein the metal is selected from titanium, vanadium or mixtures thereof, and, optionally, with at least one magnesium compound, it is possible to obtain a solid catalyst component capable of providing a bimetal catalyst for the (co)polymerization of α-olefins.

Said catalyst is capable of producing (co)polymers of α-olefins, in particular of ethylene, having various densities and molecular weights, with a good activity. Furthermore, said catalyst has good performances in the (co)polymerization of α-olefins, in particular of ethylene, at a high temperature.

An objective of the present invention therefore relates to a solid catalyst component for the (co)polymerization of α-olefins, having general formula (I)

$$Zr_n M Al_x Cl_y Mg_p \tag{I}$$

wherein:
M represents titanium (Ti), vanadium (V), or mixtures thereof;
n is a number ranging from 0.01 to 2;
x is a number ranging from 0.1 to 4;
y is a number ranging from 5 to 53;
p is a number ranging from 0 to 15;
obtained by means of a process which comprises putting the following components in contact:
(A) at least one zirconium arene having general formula (II) or (IIa) or at least one zirconium alkyl-arene having general formula (III) or (IIIc):

$$Zr(\eta^6\text{-arene})_2 Al_q X_r \tag{II}$$

$$Zr(\eta^6\text{-arene}) Al_q X_r \tag{IIa}$$

$$Zr(\eta^6\text{-arene})_2 Al_q X_r R_{s'} \tag{III}$$

$$Zr(\eta^6\text{-arene}) Al_q X_r R_{s'} \tag{IIIa}$$

wherein:
arene represents a benzene, or a benzene substituted with from 1 to 6 linear or branched $C_1$-$C_6$ alkyl groups, or mixtures thereof;
X represents a halogen atom selected from chlorine, bromine, fluorine, iodine, preferably chlorine;
R represents a linear or branched $C_1$-$C_{10}$ alkyl group;
q is a number ranging from 2 to 6, preferably 3 in the case of zirconium arene having general formula (II), 2 in the case of zirconium arene having general formula (IIa);
r is a number ranging from 8 to 20, preferably 11 in the case of zirconium arene having general formula (II), 8 in the case of zirconium arene having general formula (IIa);
q' is a number ranging from 2 to 6, preferably 3 in the case of zirconium alkyl arene having general formula (III), 2 in the case of zirconium alkyl arene having general formula (IIIa);
r' is a number ranging from 2 to 20, preferably 9 in the case of zirconium alkyl arene having general formula (III), 6 in the case of zirconium alkyl arene having general formula (IIIa);
s' is a number ranging from 2 to 6, preferably 2;
(B) at least one compound selected from:
tetrachlorides having general formula $MCl_4$ wherein M represents titanium, vanadium, or mixtures thereof;
alkoxides or chloroalkoxides having general formula $M(OR_1)_t Cl_{4-t}$ wherein M represents titanium, vanadium, or mixtures thereof, $R_1$ represents a linear or branched $C_1$-$C_{10}$ alkyl group, t is a number ranging from 1 to 4;
carboxylates or chlorocarboxylates having general formula (IV):

$$M(OOCR_2)_t Cl_{4-t} \tag{IV}$$

wherein M represents titanium, vanadium, or mixtures thereof, $R_2$ represents a linear or branched $C_1$-$C_{10}$ alkyl group, t is a number ranging from 1 to 4; or the carboxylate group $OOCR_2$ in general formula (IV) is selected from:
carboxylate groups having general formula (V):

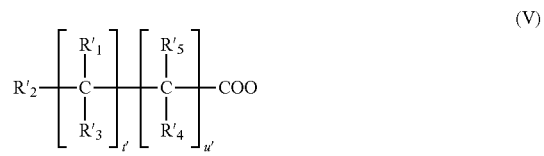

wherein $R'_1$, $R'_2$, $R'_3$, $R'_4$ and $R'_5$, each independently, represent a hydrogen atom; a halogen atom selected from chlorine, bromine, fluorine, iodine, preferably chlorine; a monofunctional hydrocarbyl radical as such or having at least one of its hydrogen atoms substituted with a halogen atom selected from chlorine, bromine, fluorine, iodine, preferably chlorine; with the proviso that at least one of the substituents from $R'_1$ to $R'_5$ represents chlorine, bromine, fluorine, iodine, preferably chlorine, or a monofunctional hydrocarbyl radical having at least one of its hydrogen atoms substituted with a halogen atom selected from chlorine, bromine, fluorine, iodine, preferably chlorine; t' and u' are numbers ranging from 0 to 10;
carboxylate groups having general formula (VI):

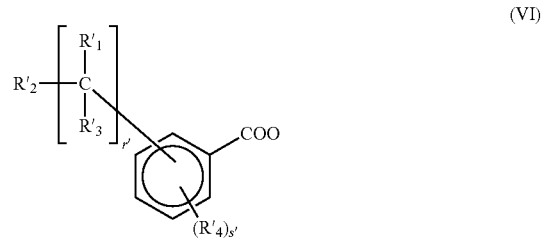

wherein $R'_1$, $R'_2$, $R'_3$ and $R'_4$, each independently, represent a hydrogen atom; a halogen atom selected from chlorine, bromine, fluorine, iodine, preferably chlorine; a monofunctional hydrocarbyl radical as such or having at least one of its hydrogen atoms substituted with a halogen atom selected from chlorine, bromine, fluorine, iodine, preferably chlorine; with the proviso that at least one of the substituents from $R'_1$ to $R'_4$ represents chlorine, bromine, fluorine, iodine, preferably chlorine, or a monofunctional hydrocarbyl radical having at least one of its hydrogen atoms substituted with a halogen atom selected from chlorine, bromine, fluorine, iodine, preferably chlorine; r' and s', each independently, are numbers ranging from 0 to 10, with the proviso that r'+s' ranges from 1 to 5;
carboxylate groups having general formula (VII):

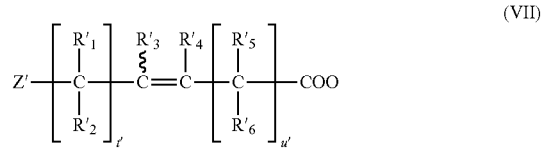

wherein $R'_1$, $R'_2$, $R'_3$, $R'_4$, $R'_5$, $R'_6$ and $Z'$, each independently, represent a hydrogen atom; a halogen atom selected from chlorine, bromine, fluorine, iodine, preferably chlorine; a monofunctional hydrocarbyl radical as such or having at least one of its hydrogen atoms substituted with a halogen atom selected from chlorine, bromine, fluorine, iodine, preferably chlorine; with the proviso that at least one of the substituents from $R'_1$ to $R'_6$ and $Z$ represents chlorine, bromine, fluorine, iodine, preferably chlorine, or a monofunctional hydrocarbyl radical having at least one of its hydrogen atoms substituted with a halogen atom selected from chlorine, bromine, fluorine, iodine, preferably chlorine; t' and u', each independently, are numbers ranging from 0 to 10, preferably between 0 and 2;

carboxylate groups having general formula (VIII):

$$R'_7\text{—COO} \qquad (VIII)$$

wherein $R'_7$ represents a monofunctional hydrocarbyl radical selected from cycloalkyls, polycycloalkyls, cycloalkenyls, polycycloalkenyls, having from 3 to 20 carbon atoms, wherein at least one of its hydrogen atoms is substituted with a halogen atom selected from chlorine, bromine, fluorine, iodine, preferably chlorine; and, optionally, (C) at least one magnesium compound selected from:
magnesium chloride ($MgCl_2$);
magnesium dialkyls having general formula $MgR_3R_4$ wherein $R_3$ and $R_4$, each independently, represent a linear or branched $C_1$-$C_{10}$ alkyl group;
complexes of magnesium chloride having general formula $MgCl_2L_u$ wherein L represents tetrahydrofuran (THF), 1,2-dimethoxyethane (DME); u is a number ranging from 1 to 4.

For the purposes of the present description and of the following claims, the definitions of the numerical ranges always include the extremes unless otherwise specified.

For the purposes of the present description and of the following claims, the term "(co)polymerization" means both the homo-polymerization of an α-olefin such as, for example, ethylene, to form high-density crystalline polyethylene or propylene to form polypropylene, and also the copolymerization of an α-olefin with at least one different unsaturated compound, copolymerizable with the same (obviously including a different α-olefin) such as, for example, the copolymerization of ethylene with ethylidene-norbornene to form a crosslinkable polyethylene, or the copolymerization of ethylene with 1-butene or with 1-hexene to form linear low density polyethylene.

For the purposes of the present description and of the following claims, the term "moles" and "molar ratio" are used with reference to compounds consisting of molecules and also with reference to atoms and ions, omitting, for the latter, the terms gram atom or atomic ratio, even if scientifically more correct.

According to a preferred embodiment of the present invention, compounds (A), (B) and, optionally (C), can be used in the following molar ratios (0.5-2):(1):(0-12), respectively.

According to a preferred embodiment of the present invention, in the zirconium arene having general formula (II) or (IIa) and/or in the zirconium alkyl arene having general formula (III) or (IIIa, said arene can be selected from: benzene, toluene, ortho-xylene, meta-xylene, para-xylene, 1,2,3-trimethylbenzene, 1,2,4-trimethylbenzene, 1,3,5-trimethylbenzene (mesitylene), hexamethylbenzene, or mixtures thereof. Benzene, toluene, 1,3,5-trimethylbenzene (mesitylene), are preferred.

According to a preferred embodiment of the present invention, in the zirconium alkyl-arene having general formula (III) or (IIIa), said group R can be selected from: ethyl, butyl, iso-butyl, n-octyl. Ethyl, butyl, n-octyl, are preferred.

Specific examples of zirconium arenes having general formula (II) or (IIa) particularly useful for the purposes of the present invention are:
$Zr(\eta^6\text{-benzene})_2Al_3Cl_{11}$;
$Zr(\eta^6\text{-benzene})_2Al_3Br_{11}$;
$Zr(\eta^6\text{-mesitylene})_2Al_3Br_{11}$;
$Zr(\eta^6\text{-mesitylene})_2Al_3Cl_{11}$;
$Zr(\eta^6\text{-benzene})Al_2Cl_8$;
$Zr(\eta^6\text{-toluene})Al_2Cl_8$;
$Zr(\eta^6\text{-mesitylene})Al_2Cl_8$;
$Zr(\eta^6\text{-benzene})Al_2Br_8$;
$Zr(\eta^6\text{-toluene})Al_2Br_8$;
$Zr(\eta^6\text{-mesitylene})Al_2Br_8$.

Specific examples of zirconium alkyl-arene having general formula (III) or (IIIa) particularly useful for the purposes of the present invention are:
$Zr(\eta^6\text{-benzene})_2Al_3Cl_9(\text{butyl})_2$;
$Zr(\eta^6\text{-benzene})_2Al_3Cl_9(\text{ethyl})_2$;
$Zr(\eta^6\text{-benzene})_2Al_3Cl_9(\text{n-octyl})_2$;
$Zr(\eta^6\text{-mesitylene})_2Al_3Cl_9(\text{butyl})_2$;
$Zr(\eta^6\text{-mesitylene})_2Al_3Cl_9(\text{ethyl})_2$;
$Zr(\eta^6\text{-mesitylene})_2Al_3Cl_9(\text{n-octyl})_2$;
$Zr(\eta^6\text{-toluene})_2Al_3Cl_9(\text{butyl})_2$;
$Zr(\eta^6\text{-toluene})_2Al_3Cl_9(\text{ethyl})_2$;
$Zr(\eta^6\text{-toluene})_2Al_3Cl_9(\text{n-octyl})_2$;
$Zr(\eta^6\text{-benzene})Al_2Cl_6(\text{n-octyl})_2$;
$Zr(\eta^6\text{-benzene})Al_2Cl_3(\text{n-octyl})_5$;
$Zr(\eta^6\text{-benzene})Al_2Cl_5(\text{n-octyl})_3$;
$Zr(\eta^6\text{-benzene})Al_2Cl_4(\text{n-octyl})_4$;
$Zr(\eta^6\text{-toluene})Al_2Cl_6(\text{n-octyl})_2$;
$Zr(\eta^6\text{-toluene})Al_2Cl_3(\text{n-octyl})_5$;
$Zr(\eta^6\text{-toluene})Al_2Cl_5(\text{n-octyl})_3$;
$Zr(\eta^6\text{-toluene})Al_2Cl_4(\text{n-octyl})_4$;
$Zr(\eta^6\text{-mesitylene})Al_2Cl_6(\text{n-octyl})_2$;
$Zr(\eta^6\text{-mesitylene})Al_2Cl_3(\text{n-octyl})_5$;
$Zr(\eta^6\text{-mesitylene})Al_2Cl_5(\text{n-octyl})_3$;
$Zr(\eta^6\text{-mesitylene})Al_2Cl_4(\text{n-octyl})_4$;
$Zr(\eta^6\text{-benzene})Al_2Cl_6(\text{butyl})_2$;
$Zr(\eta^6\text{-benzene})Al_2Cl_3(\text{butyl})_5$;
$Zr(\eta^6\text{-benzene})Al_2Cl_5(\text{butyl})_3$;
$Zr(\eta^6\text{-benzene})Al_2Cl_4(\text{butyl})_4$;
$Zr(\eta^6\text{-toluene})Al_2Cl_6(\text{butyl})_2$;
$Zr(\eta^6\text{-toluene})Al_2Cl_3(\text{butyl})_5$;
$Zr(\eta^6\text{-toluene})Al_2Cl_5(\text{butyl})_3$;
$Zr(\eta^6\text{-toluene})Al_2Cl_4(\text{butyl})_4$;
$Zr(\eta^6\text{-mesitylene})Al_2Cl_6(\text{butyl})_2$;
$Zr(\eta^6\text{-mesitylene})Al_2Cl_3(\text{butyl})_5$;
$Zr(\eta^6\text{-mesitylene})Al_2Cl_5(\text{butyl})_3$;
$Zr(\eta^6\text{-mesitylene})Al_2Cl_4(\text{butyl})_4$;
$Zr(\eta^6\text{-benzene})Al_2Cl_6(\text{ethyl})_2$;
$Zr(\eta^6\text{-benzene})Al_2Cl_3(\text{ethyl})_5$;
$Zr(\eta^6\text{-benzene})Al_2Cl_5(\text{ethyl})_3$;
$Zr(\eta^6\text{-benzene})Al_2Cl_4(\text{ethyl})_4$;
$Zr(\eta^6\text{-toluene})Al_2Cl_6(\text{ethyl})_2$;
$Zr(\eta^6\text{-toluene})Al_2Cl_3(\text{ethyl})_5$;
$Zr(\eta^6\text{-toluene})Al_2Cl_5(\text{ethyl})_3$;
$Zr(\eta^6\text{-toluene})Al_2Cl_4(\text{ethyl})_4$;
$Zr(\eta^6\text{-mesitylene})Al_2Cl_6(\text{ethyl})_2$;
$Zr(\eta^6\text{-mesitylene})Al_2Cl_3(\text{ethyl})_5$;
$Zr(\eta^6\text{-mesitylene})Al_2Cl_5(\text{ethyl})_3$;
$Zr(\eta^6\text{-mesitylene})Al_2Cl_4(\text{ethyl})_4$.

According to a preferred embodiment of the present invention, said tetrachlorides having general formula $MCl_4$ can be selected from: titanium tetrachloride, vanadium tetrachloride, or mixtures thereof.

According to a preferred embodiment of the present invention, said alkoxides or chloroalkoxides having general formula $M(OR_1)_tCl_{4-t}$ can be selected from: titanium or vanadium tetra-ethoxide; titanium or vanadium tetra-propoxide; titanium or vanadium tetra-n-butoxide; titanium or vanadium tetra-iso-butoxide; or their relative chlorides; or mixtures thereof.

According to a preferred embodiment of the present invention, said carboxylate groups having general formula (V) can be selected from: $CCl_3COO$, $CCl_3CH_2COO$, $CCl_3(CH_2)_2COO$, $CHCl_2COO$, $CH_3CCl_2COO$, $C_6H_5CCl_2CH_2COO$, $(C_6H_5)_2CClCOO$, $CH_3CH_2CCl_2COO$, $C_6H_5(CH_2)_3CHClCOO$, $ClC_6H_4CHClCOO$, $ClC_6H_4CH_2COO$, 2-cyclopropyl-2,2-dichloroacetate, or mixtures thereof.

According to a preferred embodiment of the present invention, said carboxylate groups having general formula (VI) can be selected from: $Cl_3CC_6H_4COO$, $ClCH_2C_6H_4COO$, $ClCH_2C_6H_2Cl_2COO$, $C_6Cl_5COO$, or mixtures thereof.

According to a preferred embodiment of the present invention, said carboxylate groups having general formula (VII) can be selected from: $CCl_3CH=COO$, $CCl_3CCl=CClCOO$, $CCl_2=CClCCl_2COO$, or mixtures thereof.

According to a preferred embodiment of the present invention, said carboxylate groups having general formula (VIII) can be selected from: 2-chloro-cyclohexane-carboxylate, 2,2-dichlorocyclopropane-carboxylate, 2,2,3,3-tetrachloropropane-carboxylate, perchloro-cyclohexane-carboxylate, cyclo-hex-2-ene-2-trichloro-methyl-carboxylate, or mixtures thereof.

According to a preferred embodiment of the present invention, said carboxylates or chlorocarboxylates having general formula (IV) can be selected from: titanium or vanadium tetra-n-decanoate; titanium or vanadium tetra-n-undecanoate; titanium or vanadium tetra-iso-butyrate; titanium or vanadium tetra-2-ethyl-hexanoate; titanium or vanadium tetra-2,2-dimethylpropanoate; titanium or vanadium tetra-versatate; titanium or vanadium tetra-3-ethyl-pentanoate; titanium or vanadium tetra-citronellate; titanium or vanadium tetra-naphthenate; titanium or vanadium tetra-2-phenyl-butyrate; or their relative chlorides; or mixtures thereof.

According to a preferred embodiment of the present invention, said magnesium dialkyls having general formula $MgR_3R_4$ can be selected from: magnesium butyl-octyl [$(n-C_4H_9)_{1.5}(n-(C_8H_{17})_{0.5}Mg$], magnesium ethyl-butyl [$(n-C_2H_5)(n-(C_4H_9)Mg$], magnesium di-butyl [$n-(C_4H_9)_2Mg$], or mixtures thereof.

According to a preferred embodiment of the present invention, said magnesium chloride complexes having general formula $MgCl_2L_u$ can be selected from: magnesium-tetrahydrofuran chloride complex, magnesium 1,2-dimethoxyethane chloride complex, magnesium-pyrane chloride complexes, magnesium-ethylether chloride complexes, magnesium-dioctylether chloride complexes, magnesium-dibutylether chloride complexes, or mixtures thereof.

In order to improve the catalytic activity of the catalyst comprising the solid catalyst component object of the present invention, said process can include the use of an organic chloro-derivative as activator.

According to a further embodiment of the present invention, said process comprises putting components (A), (B) and, optionally, (C), in contact with at least one organic chloro-derivative (D) which can be selected from:

(a) di- or poly-chloroalkanes;
(b) alkyl esters of aliphatic carboxylic acids di- or tri-chloro-substituted on the carbon in alpha position with respect to the carboxyl;
(c) monochloro triphenylmethane or dichloro diphenylmethane carrying a carboxyalkyl group in para position of at least one of the phenyl rings.

According to a preferred embodiment of the present invention, said di- or poly-chloro alkanes (a) can be selected from:
dichloromethane;
α-β-dichloroalkanes having general formula:

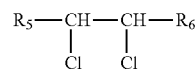

wherein $R_5$ and $R_6$, each independently, represent a hydrogen atom, or a linear or branched $C_1$-$C_{10}$, preferably $C_1$-$C_5$, alkyl group;
α-ω-dichloroalkanes having general formula:

wherein v is an integer ranging from 1 to 10, preferably ranging from 1 to 5;
trichloroalkanes and tetrachloroalkanes carrying the chlorine atoms on the two terminal carbons having general formula:

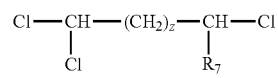

wherein $R_7$ represents a halogen atom, preferably chlorine; z is an integer ranging from 1 to 10, preferably ranging from 1 to 5;
trichloroalkanes carrying the chlorine atoms on a terminal carbon having general formula:

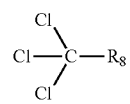

wherein $R_8$ represents a linear or branched $C_1$-$C_{10}$, preferably $C_1$-$C_5$, alkyl group.

Specific examples of di- or poly-chloroalkanes (a) particularly useful for the purposes of the present invention are: 1,2-dichloroethane, 1,3-trichloropropane, 1,4-dichlorobutane, 2,3-dichlorobutane, 1,4-dichloropentane, 1,6-dichlorohexane, 1,1,1-trichloroethane, 1,1,2-trichloroethane, or mixtures thereof. 1,2-Dichloroethane, 2,3-dichlorobutane, or mixtures thereof, are preferred.

According to a preferred embodiment of the present invention, said alkyl esters of aliphatic carboxylic acids di- or tri-chloro-substituted on the carbon in alpha position with respect to the carboxyl (b) are selected from those having the following general formula:

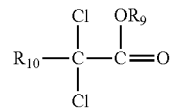

wherein $R_9$ represents a hydrogen atom, a chlorine atom, or a linear or branched $C_1$-$C_{10}$, preferably $C_1$-$C_5$, alkyl group; $R_{10}$ represents a linear or branched $C_1$-$C_{10}$, preferably $C_1$-$C_5$, alkyl group.

Specific examples of alkyl esters of aliphatic carboxylic acids di- or tri-chloro-substituted on the carbon in alpha position with respect to the carboxyl (b) particularly useful for the purposes of the present invention are methyl and ethyl esters of 1,1-dichloroacetic acid and 1,1,1-trichloroacetic acid, or mixtures thereof.

According to a preferred embodiment of the present invention, said monochloro triphenylmethane or dichloro diphenylmethane carrying a carboxyalkyl group in para position of at least one of the phenyl rings (c) can be selected from those having general formula:

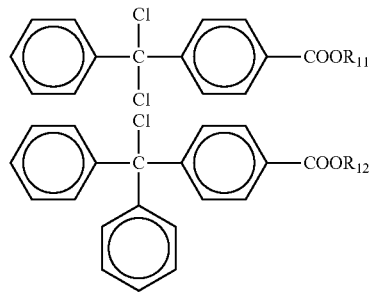

wherein $R_{11}$ and $R_{12}$, each independently, represent a linear or branched $C_1$-$C_{10}$, preferably $C_1$-$C_5$, alkyl group.

Specific examples of said monochloro triphenylmethane or dichloro diphenylmethane carrying a carboxyalkyl group in para position of at least one of the phenyl rings (c) particularly useful for the purposes of the present invention are those corresponding to the above-mentioned formulae in which $R_{11}$ and $R_{12}$, each independently, represent a methyl or ethyl group.

According to a preferred embodiment of the present invention, compounds (A), (B) and, optionally, (C) and/or (D), can be used in the following molar ratios (0.5-2):(1):(0-12):(0-40), respectively.

In order to improve the catalytic activity of the catalyst comprising the solid catalyst component object of the present invention, said process in addition can comprise the use of an aluminium alkyl as activator.

According to a preferred embodiment of the present invention, said process comprises putting components (A), (B) and, optionally, (C) and/or (D), in contact with at least one aluminium alkyl chloride (E) which is selected from those having general formula $$Al(R_{13})_w Cl_{3-w}$$

wherein $R_{13}$ represents a linear or branched $C_1$-$C_{20}$, preferably $C_1$-$C_{18}$, alkyl group; w is 1 or 2.

Specific examples of aluminium alkyl chlorides (E) particularly useful for the purposes of the present invention are: di-ethyl-aluminium chloride, mono-ethyl-aluminium dichloride, di-methyl-aluminium chloride, di-isobutyl-aluminium chloride, iso-butyl-aluminium dichloride, ethyl-aluminium sesquichloride, or mixtures thereof.

According to a preferred embodiment of the present invention, compounds (A), (B) and, optionally, (C) and/or (D) and/or (E), can be used in the following molar ratios (0.5-2):(1):(0-12):(0-40):(0-40), respectively.

The solid catalyst component having general formula (I) object of the present invention, can be obtained according to processes known in the art.

Generally, a solution (A) of zirconium arene having general formula (II) or (IIa) or of zirconium alkyl-arene having general formula (III) or (IIIa), previously isolated from the reaction raw material, or a reaction raw material (biphasic system) containing zirconium arene having general formula (II) or (IIa) or zirconium alkyl-arene having general formula (III) or (IIIa), is put in contact with components (B) and, optionally, (C), and/or (D), and/or (E), in solution or in suspension. The solvents suitable for this purpose can be selected from inert, non-reactive organic solvents, preferably aliphatic or aromatic hydrocarbon solvents such as, for example, n-pentane, n-hexane, n-heptane, n-octane, n-nonane, n-decane, n-undecane, n-dodecane, benzene, toluene, xylene, 1,3,5-trimethyl benzene (mesitylene), more preferably in the solvent corresponding to the arene present in the compounds of general formula (II), (IIa), (III) or (IIIa). The reaction is normally carried out under stirring, at room temperature, or at a temperature higher than room temperature, for example up to approximately the boiling point of the solvent used or at the reflux temperature of the mixture obtained by putting the above components in contact, for a period of time ranging from 2 hours to 15 hours, preferably at room temperature for about 15 hours, to cause the precipitation of the solid catalyst component in the form of a granular solid. The dispersion, or solution, of the solid catalyst component in the relative solvent, thus obtained, can be used directly in the (co)polymerization process of $\alpha$-olefins (e.g., of ethylene). Alternatively, the solid catalyst component can be previously separated from its dispersion, subjected to washing with an organic hydrocarbon solvent (for example, n-pentane, n-hexane, n-heptane) and dried.

For the purposes of the present description and of the following claims, the term "room temperature" means a temperature ranging from 20° C. to 25° C.

According to a further embodiment of the present invention, said solid catalyst component having general formula (I) can also be in supported form on an inert solid, preferably having a controlled and narrow particle-size distribution. Suitable inert solids are those which do not modify the characteristics of the catalytic part mentioned above, the ratios between the different elements present, and the specific coordinative characteristics of zirconium. Examples of these solids are in-organic solids such as silicon and aluminium oxides, mixed silica-alumina oxides, titanium oxide, silicates, silicoaluminates, zeolites, and similar products. Organic polymeric solids can also be used as carrier, such as certain types of functionalized polystyrene. Preferred solids are: silica, alumina (in its different forms), amorphous or crystalline silicoaluminates (zeolites). The amount of inert carrier is normally selected so that it forms from 50% by weight to 90% by weight of the resulting supported solid component. These supported solid components are particularly suitable for gas phase polymerization processes.

The inert solid carrier can be introduced, in the desired quantity according to the present invention, together with the above-mentioned components (A), (B), and, optionally, (C) and/or (D) and/or (E), in solution or in suspension, so that the solid catalyst component then precipitates on the surface of the inert carrier, favouring a homogeneous distribution of the same. Alternatively, said carrier can be impregnated with a solution of the solid catalyst component having general formula (I) to induce the precipitation of said solid component with a more homogeneous distribution on the inert carrier.

A further aspect of the present invention relates to a catalyst for the (co)polymerization of α-olefins comprising the solid component described above.

According to a further aspect, the present invention relates to a catalyst for the (co)polymerization of α-olefins comprising:
a solid catalyst component having general formula (I):

$$Zr_nMAl_xCl_yMg_p \qquad (I)$$

wherein:
M represents titanium (Ti), vanadium (V), or mixtures thereof;
n is a number ranging from 0.01 to 2;
x is a number ranging from 0.1 to 4;
y is a number ranging from 5 to 53;
p is a number ranging from 0 to 15;
a co-catalyst selected from aluminium alkyls having general formula:

$$Al(R_{13})_wCl_{3-w}$$

wherein $R_{13}$ represents a linear or branched $C_1$-$C_{20}$, preferably $C_1$-$C_{18}$, alkyl group; w is 1, 2 or 3.

Specific examples of co-catalysts particularly suitable for the purposes of the present invention are: tri-ethyl-aluminium, tri-n-butyl-aluminium, tri-iso-butyl-aluminium, tri-hexyl-aluminium, di-ethyl-aluminium chloride, mono-ethyl-aluminium dichloride, di-methyl-aluminium chloride, di-isobutyl-aluminium chloride, iso-butyl-aluminium dichloride, ethyl-aluminium sesquichloride, or mixtures thereof. Tri-ethyl-aluminium, tri-n-butyl-aluminium, tri-iso-butyl-aluminium, tri-hexyl-aluminium, or mixtures thereof, are particularly preferred. Tri-ethyl-aluminium, tri-iso-butyl-aluminium are particularly preferred.

According to a preferred embodiment of the present invention, in said catalyst, the molar ratio between the aluminium present in the co-catalyst and the titanium and/or vanadium present in the solid catalyst component having general formula (I), can range from 0.5 to 200.

Said catalyst can be obtained according to known techniques. Said catalyst can be obtained, for example, by contact of the solid catalyst component having general formula (I) and the co-catalyst, preferably in a suitable liquid medium, normally a hydrocarbon, which can also consist of, or can contain, one or more of the α-olefins to be (co)polymerized. Depending on the characteristics of the (co)polymerization process in which the catalyst of the present invention is to be used, the latter can be prepared separately and subsequently introduced into the polymerization reactor, or it can be prepared in situ, by feeding the components separately to the reactor. The temperature at which the catalyst is prepared is not particularly critical, it can vary within a large range and normally ranges from 0° C. to the operating temperature of the catalyst in the (co)polymerization process. The formation of the catalyst is normally almost immediate already at room temperature, even if, in certain cases, contact between the components can be maintained for a period ranging from 10 seconds to 30 minutes, depending on the temperature, before starting the (co)polymerization.

One or more additives or further components can be optionally added to the above-mentioned catalyst according to the present invention, to obtain a catalytic system suitable for satisfying specific practical requirements. The catalytic systems thus obtained should be considered as being included in the scope of the present invention. Additives or components which can be included in the preparation and/or formulation of the catalyst of the present invention are inert solvents, such as, for example, aliphatic and/or aromatic hydrocarbons, aliphatic and aromatic ethers, weakly coordinated additives (Lewis bases) selected, for example, from non-polymerizable olefins, ethers, tertiary amines and alcohols, halogenating agents such as silicon halides, halogenated hydrocarbons, preferably chlorinated, and similar products, and also all the other optional components normally used in the art for the preparation of traditional catalysts for the (co)polymerization of both ethylene and other α-olefins.

The present invention also relates to a (co)polymerization process of α-olefins characterized in that it uses said catalyst.

The catalyst according to the present invention can be used with excellent results in substantially all the known (co)polymerization processes of α-olefins, either in continuous or batchwise, in one or more steps, such as, for example, processes at low (0.1 MPa-1.0 MPa), medium (1.0 MPa-10 MPa), or high (10 MPa-150 MPa) pressure, at temperature ranging from 20° C. to 300° C., optionally in the presence of an inert diluent. Hydrogen can be suitably used as molecular weight regulator.

Said processes can be carried out in solution or in suspension in a liquid diluent which can be selected, for example, from aliphatic or cycloaliphatic saturated hydrocarbons having from 3 to 12, preferably from 6 to 10 carbon atoms, but which can also be a monomer, such as, for example, in the known copolymerization process of ethylene and propylene in liquid propylene. The quantity of catalyst introduced into the (co)polymerization mixture is preferably selected so that the titanium and/or the vanadium concentration present in the catalyst ranges from $10^{-4}$ moles/liter to $10^{-8}$ moles/liter.

Alternatively, the (co)polymerization can be carried out in gas phase, for example in a fluid bed reactor, normally at pressures ranging from 0.5 Mpa to 5 MPa, and at temperatures ranging from 50° C. to 150° C., it being preferable in this case for the solid catalyst component having general formula (I) object of the present invention, to be of the type supported on an inert carrier, as previously described.

The α-olefins which can be used in the above-mentioned processes are preferably those containing from 2 to 20, more preferably from 2 to 8, carbon atoms, aliphatic, cycloaliphatic or aromatic, such as, for example, ethylene, propylene, 1-butene, 4-methylpent-1-ene, 1-hexene, 1-octene, ethylidene-norbornene, styrene, or mixtures thereof. Ethylene is particularly preferred, for both homo- and co-polymerization, wherein ethylene is, in any case, the prevailing monomer.

The catalyst object of the present invention can also be used with excellent results in the polymerization of ethylene to give linear polyethylene and in the copolymerization of ethylene with propylene or with higher α-olefins, preferably having from 4 to 10 carbon atoms, to give copolymers having different characteristics depending on the specific polymerization conditions and the quantity and structure of the same α-olefin. Linear polyethylenes can be obtained, for example, having a density ranging from 0.880 to 0.940, and with average molecular weights preferably ranging from 100,000 to 2,000,000. The α-olefins preferably used as co-monomers of ethylene in the production of linear low- or medium-density polyethylene (known as ULDPE, VLDPE and LLDPE, depending on the density), are 1-butene, 1-hexene, 1-octene.

The catalyst object of the present invention can also be suitably used in copolymerization processes of ethylene and propylene to give saturated elastomeric polymers which can be vulcanized by means of peroxides, extremely resistant to aging and degradation, or in the terpolymerization of ethylene, propylene and a non-conjugated diene having from 5 to 20 carbon atoms, to obtain vulcanizable rubbers of the EPDM type.

Examples of non-conjugated dienes typically used for preparing these copolymers are 5-ethylidene-2-norbornene (ENB), 1,4-hexadiene, 1,6-octadiene.

The catalyst object of the present invention can also be suitably used in (co)polymerization processes of α-olefins and, in particular, of ethylene, in solution, at a high temperature. These processes are normally carried out at temperatures ranging from 130° C. to 300° C. and at a pressure ranging from 1 MPa to 25 MPa, preferably ranging from 5 Mpa to 20 MPa, in the presence of an inert liquid capable of maintaining the polymer formed in solution, at the process temperature. In this way, a homogeneous reaction mixture (except for the catalyst) and an easily controllable and flexible process, which allows short residence times and high productivities, are obtained. Preferred liquids both for their solvation characteristics of the polyolefins and also for their relatively low toxicity, are aliphatic or cycloaliphatic hydrocarbons having from 6 to 10 carbon atoms such as, for example, heptane, decane, cyclohexane, decalin. The polymer is then separated by precipitation or devolatization of the solvent. For general information on known processes of this type, reference should be made, among the numerous publications available, to Encyclopaedia of Polymer Science and Engineering", $2^a$ edition (1986), Vol. 6, pages 471-472, John Wiley & Sons Ed.

As polyolefins, especially if semi-crystalline, have a poor solubility in solvents, the use of relatively high temperatures, preferably ranging from 150 to 230° C., is critical in carrying out these processes. The processes are carried out in adiabatic or isothermal reactors, depending on the technology used. It is known, however, that in (co)polymerization processes at such high temperatures, the average molecular weight of the polymer obtained decreases significantly, leading to "Melt Flow Index" (MFI) levels which are so high as to be unacceptable for usual transformation processes. The catalysts normally used in solution processes are based on vanadium, they are not capable, however, of producing polyolefins having satisfactory molecular weights for a large range of applications, and this limits the diffusion of this process, in spite of the above-mentioned advantages. Furthermore, there is room for further improvement also with respect to the activity of these catalysts. The known Ziegler-Natta catalysts based on titanium, normally used in suspension processes, on the other hand, have proved to be even less suitable than the previous ones when used at high temperatures, producing polyethylenes with particularly low molecular weights, unsuitable for most of the normal applications.

The catalyst according to the present invention unexpectedly allows high average molecular weights of ethylene polymers and copolymers to be obtained, also operating at the above-mentioned high temperatures, obtaining much lower "Melt Flow Index" (MFI) values (even by an order of magnitude) with respect to the traditional catalysts used under the same process conditions.

The zirconium arene having general formula (II) or (IIa) can be obtained by means of processes known in the art as described, for example, by Troyanov et al. in "Synthesis of arene Ti and Zr complexes and their reactivity towards air: crystal structure of $[(C_6H_3Me_3)_2Zr(AlCl_4)](Al_2Cl_7)$ and $TiCl_3(OPh)$", *Journal of Organometallic Chemistry* (1995), Vol. 494, C4-C7; or in "The synthesis and crystal structure of the π-benzenezirconium(III) bromoaluminate complex {(μ$_2$-Br)$_3$[(η-C$_6$H$_6$)Zr(μ$_2$-Br)$_2$.AlBr$_2$]$_2$}(Al$_2$Br$_7$).2.5C$_6$H$_6$ and the π-benzene-zirconium(II) iodoaluminate complex [(η-C$_6$H$_6$)$_2$Zr(μ$_2$-I)$_2$AlI$_2$](Al$_3$I$_{10}$).0.5C$_6$H$_6$", *Organometallic Chemistry in the USSR* (1989), Vol. 2(6), pg. 732-736; or in "The synthesis and crystal structure of the π-mesitylenezirconium(II) bromide complexes [(η$^6$-C$_6$H$_3$Me$_3$)$_2$Zr(μ-Br)$_2$AlBr$_2$].(Al$_2$Br$_7$) and [(η$^6$-C$_6$H$_3$Me$_3$)$_2$Zr(μ-Br)$_2$.AlBr$_2$](Al$_3$OBr$_8$)", *Organometallic Chemistry in the USSR* (1992), Vol. 5(5), pg. 527-530; "Arene Complexes of Titanium and Zirconium in Low Oxidation States: Crystal Structures of β-(η$^6$-C$_6$H$_6$)Ti(AlI$_4$)$_2$, [η$^6$-(C$_6$Me$_6$)$_3$Zr$_3$Br$_6$](Al$_2$OBr$_8$)(Al$_2$Br$_7$).(C$_6$H$_6$) [η$^6$-C$_6$H$_3$Me$_3$)$_3$Zr$_3$Br$_6$](Al$_3$OBr$_8$)$_3$, and [(η$^6$-C$_6$H$_6$)$_2$Zr(AlBr$_4$)](Al$_2$Br$_7$).2(C$_6$H$_6$)," *Russian Journal of Coordination Chemistry* (1997), Vol. 23, No. 12, pages 836-843.

Said zirconium arene having general formula (II) or (IIa) can be obtained, for example, by putting the following components in contact, under the reaction conditions: aluminium metal, aluminium trichloride, zirconium tetrachloride and the arene selected. At the end of the reaction a biphasic system is obtained (reaction raw material) which can be filtered to eliminate the aluminium metal, unaltered and in excess, obtaining a solution from which said zirconium arene, in the form of a solid, is separated, for example, by precipitation in a hydrocarbon solvent, preferably aliphatic (e.g., n-heptane).

For the purposes of the present invention and of the following claims, the wording "at least one zirconium arene having general formula (II) or (IIa)" means that it is possible to use either a zirconium arene in solid form, or the biphasic system (reaction raw material) obtained in the preparation process of said zirconium arene having general formula (II) or (IIa), which can be filtered to eliminate the excess of aluminium metal, or non-filtered, containing said zirconium arene having general formula (II) or (IIa).

It should be noted that the zirconium arene having formula:

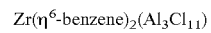

$$Zr(\eta^6\text{-benzene})_2(Al_3Cl_{11})$$

has not been described in the art.

A further object of the present invention therefore relates to a zirconium arene having formula

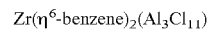

$$Zr(\eta^6\text{-benzene})_2(Al_3Cl_{11})$$

In a further aspect, the present invention relates to a zirconium alkyl-arene having general formula (III) or (IIIa):

$$Zr(\eta^6\text{-arene})_2Al_{q'}X_{r'}R_{s'} \tag{III}$$

$$Zr(\eta^6\text{-arene})Al_{q'}X_{r'}R_{s'} \tag{IIIa}$$

wherein:

arene represents a benzene, or a benzene substituted with from 1 to 6 linear or branched $C_1$-$C_6$ alkyl groups, or mixtures thereof;

X represents a halogen atom selected from chlorine, bromine, fluorine, iodine, preferably chlorine;

R represents a linear or branched $C_1$-$C_{10}$ alkyl group;

q' is a number ranging from 2 to 6, preferably 3 in the case of zirconium alkyl-arene having general formula (III), 2 in the case of zirconium alkyl-arene having general formula (IIIa);

r' is a number ranging from 2 to 20, preferably 9 in the case of zirconium alkyl-arene having general formula (III), 6 in the case of zirconium alkyl-arene having general formula (IIIa);

s' is a number ranging from 2 to 6, preferably 2.

In a further embodiment, the present invention also relates to a process for the preparation of a zirconium alkyl-arene having general formula (III) or (IIIa), which comprises putting the following components in contact:

(i) at least one zirconium arene having general formula (II) or (IIa):

$$Zr(\eta^6\text{-arene})_2Al_qCl_r \tag{II}$$

$$Zr(\eta^6\text{-arene})Al_qCl_r \tag{IIa}$$

wherein:
arene represents a benzene, or a benzene substituted with from 1 to 6 linear or branched $C_1$-$C_6$ alkyl groups, or mixtures thereof;
X represents a halogen atom selected from chlorine, bromine, fluorine, iodine, preferably chlorine;
q is a number ranging from 2 to 6, preferably 3 in the case of zirconium arene having general formula (II), 2 in the case of zirconium arene having general formula (IIa);
r is a number ranging from 8 to 20, preferably 11 in the case of zirconium arene having general formula (II), 8 in the case of zirconium arene having general formula (IIa);
(ii) at least one alkylation agent selected from:
metal alkyls having general formula

wherein M represents aluminium, magnesium, zinc, lithium; $R_{16}$ represents a linear or branched $C_1$-$C_{12}$, preferably $C_1$-$C_{10}$, alkyl group; b is 1, 2 or 3;
aluminium alkyl chlorides having general formula:

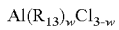

wherein $R_{13}$ represents a linear or branched $C_1$-$C_{20}$ preferably $C_1$-$C_{18}$, alkyl group; w is 1 or 2.

Specific examples of metal alkyls particularly useful for the purposes of the above-mentioned process are: lithium n-butyl, lithium sec-butyl, lithium t-butyl, lithium n-pentyl, aluminium tri-ethyl, aluminium tri-iso-butyl, aluminium tri-octyl, butyl-octyl-magnesium, di-butyl-magnesium, butyl-hexyl-magnesium, or mixtures thereof.

Specific examples of aluminium alkyl chlorides particularly useful for the purposes of the above-mentioned process are: di-ethyl-aluminium chloride, mono-ethyl-aluminium dichloride, di-methyl-aluminium chloride, di-isobutyl-aluminium chloride, iso-butyl-aluminium dichloride, ethyl-aluminium sesquichloride, or mixtures thereof.

According to a preferred embodiment of the present invention, said reaction can be carried out in the presence of an organic solvent, preferably an aliphatic or aromatic hydrocarbon solvent such as, for example, n-pentane, n-hexane, n-heptane, n-octane, n-nonane, n-decane, n-undecane, n-dodecane, benzene, toluene, xylene, 1,3,5-trimethylbenzene (mesitylene). The reaction is normally carried out under stirring, at room temperature, or at a temperature higher than room temperature, for example up to approximately the boiling point of the solvent used or at the reflux temperature of the mixture obtained by putting the above components in contact, for a time ranging from 2 hours to 24 hours, preferably at room temperature for about 24 hours, or at the reflux temperature of said mixture for a time ranging from 2 hours to 6 hours, to cause the precipitation of the zirconium alkyl-arene in the form of a granular solid, or a solution comprising said zirconium alkyl-arene can be obtained.

For the purposes of the present invention and of the following claims, the wording "at least one zirconium alkyl-arene having general formula (III) or (IIIa)" means that either a zirconium alkyl-arene in solid form, or the solution (reaction raw material) obtained in the preparation process of said zirconium alkyl-arene having general formula (III) or (IIIa), which can be filtered to eliminate the excess of aluminium metal, or non-filtered, containing said zirconium alkyl-arene having general formula (III) or (IIIa), can be used.

Some illustrative and non-limiting examples are provided hereunder for a better understanding of the present invention and for its embodiment.

EXAMPLES

Reagents and Materials

The reagents and materials used in the following examples of the invention are listed hereunder together with their optional pre-treatments and their manufacturer:
zirconium tetrachloride ($ZrCl_4$) (Aldrich, 99.9%): used as such;
anhydrous aluminium trichloride ($AlCl_3$) (Fluka): used as such;
benzene (Aldrich): pure, ≥99%, distilled on sodium (Na) in an inert atmosphere;
mesitylene (Aldrich): pure, ≥99%, distilled on sodium (Na) in an inert atmosphere;
toluene (Aldrich): pure, ≥99%, distilled on lithium aluminium hydride ($LiAlH_4$) in an inert atmosphere;
aluminium metal (Carlo Erba RPE): powder, used as such;
aluminium tri-octyl [Al(octyl)$_3$] (Aldrich): used as such;
titanium tetrachloride ($TiCl_4$) (Fluka): pure, ≥99%, distilled in an inert atmosphere;
vanadium tetrachloride ($VCl_4$) (Fluka): pure, ≥99%, used as such;
anhydrous magnesium chloride ($MgCl_2$) (Cezus-Areva): >99%, grade T.202, used as such;
complex magnesium-tetrahydrofuran chloride [$MgCl_2$(THF)$_2$] prepared according to the description of Oche̊ dzan-Siodlak et al. in "Magnesium chloride modified with organoaluminium compounds as a support of the zircocene catalyst for ethylene polymerization", *European Polymer Journal* (2004), Vol. 40, pages 839-846;
magnesium-1,2-dimethoxyethane [$MgCl_2$(DME)$_2$]chloride complex prepared according to the description of Neumueller et al. in "Crystal structure of $MgCl_2$(1,2-dimethoxyethane)$_2$", *Zeitschrift für Naturforschung. B* (1993), Vol. 48, No. 8, pages 1151-1153;
butyl-octyl magnesium [(n-$C_4H_9$)$_{1.5}$(n-($C_8H_{17}$)$_{0.5}$Mg] (Chemtura): used as such;
n-decane: pure, ≥95%, (Synthesis—Parma), treated on molecular sieves 4 Å and 10 Å, of Grace Davison;
n-heptane (Carlo Erba, RPE): anhydryfied by distillation on sodium(Na) in an inert atmosphere;
n-pentane (Carlo Erba, RPE): anhydryfied by distillation on sodium (Na) in an inert atmosphere;
n-hexane (Carlo Erba, RPE): anhydryfied by distillation on sodium (Na) in an inert atmosphere;
tert-butylchloride (Acros): used as such;
tri-iso-butyl aluminium (TIBAL) (Chemtura): used as such;
ethylene: Rivoira Grade 3.5, purity≥99.95%;
1-hexene: 97%, Aldrich, distilled on calcium hydride;
di-ethyl-aluminium chloride (DEAC) (Chemtura, pure): used as such;
2,3-dichlorobutane (Acros): used as such;
methanol (Acros): acidified by addition of an aqueous solution of hydrochloric acid (HCl) at 37%;
tetrahydrofuran (THF) (Carlo ERBA, RPE): anhydryfied by distillation on lithium aluminium hydride ($LiAlH_4$) in an inert atmosphere.

The analyses and characterization methods listed below were used.

Elemental Analysis a) Determination of Mg, Al, Zr, Ti and V

For the determination of the weight quantity of the metals Mg, Al, Zr, Ti and V, in the solid catalyst components object of the present invention, an aliquot weighed exactly, operating in a dry-box under a nitrogen flow, of about 30 mg-50 mg of sample, was placed in a platinum crucible of about 30 ml, together with a mixture of 1 ml of hydrofluoric acid (HF) at 40%, 0.25 ml of sulfuric ($H_2SO_4$) at 96% and 1 ml of nitric acid ($HNO_3$) at 70%. The crucible was then heated on a plate, increasing the temperature until the appearance of white sulfuric fumes (about 200° C.). The mixture thus obtained was cooled to room temperature, 1 ml of nitric acid ($HNO_3$) at 70% was added and the mixture was then heated until the appearance of fumes. After repeating the above sequence a further two times, a limpid, almost colourless solution was obtained. 1 ml of nitric acid ($HNO_3$) and about 15 ml of water were then cold-added and the mixture was then heated to 80° C., for about 30 minutes. The sample thus prepared was diluted with water having a MilliQ purity up to a weight of about 50 g, weighed exactly, to obtain a solution on which analytical, instrumental determination was carried out using an ICP-OES (optical detection plasma) Thermo Optek IRIS Advantage Duo spectrometer, by comparison with solutions at a known concentration. For this purpose, a calibration curve was prepared for each analyte, within the range of 0-10 ppm, measuring solutions having a known titre obtained by weight dilution of certified solutions.

The solution of the sample prepared as described above was diluted again by weight so as to obtain concentrations close to those used as reference, before carrying out spectrophotometric analysis. All the samples were prepared in duplicate. The results were considered acceptable if the single data of the tests in duplicate did not differ by more than 2% relative with respect to their average value.

b) Chlorine Determination

For said purpose, samples of the solid catalyst components object of the present invention, about 30 mg-50 mg, were weighed exactly in 100 ml glasses in a dry-box under a stream of nitrogen. 2 g of sodium carbonate ($Na_2CO_3$) were added and 50 ml of MilliQ water were added, outside the dry-box. It was brought to boiling point on a plate, under magnetic stirring, for about 30 minutes. It was left to cool, diluted $H_2SO_4$ 1/5 was added until the reaction became acid and the mixture was titrated with silver nitrate ($AgNO_3$) 0.1 N with a potentiometer titrimeter.

UV-Vis Spectroscopy

The UV-Vis analysis was carried out using a Perkin-Elmer Λ-19 double-beam spectrophotometer, with scanning within the range of 300 nm to 850 nm and resolution at 0.5 nm. For said purpose, samples of the solid catalyst components object of the present invention, were dissolved in the appropriate solvent at the desired molar concentration, they were placed in a Suprasil quartz cuvette, filled and stoppered operating under a strictly inert atmosphere (dry-box in an argon atmosphere), and were analyzed in diffused reflectance by means of an integrating sphere. The solutions being examined (about 3 ml) were introduced with the Schlenk technique in an anhydrified argon or nitrogen atmosphere into cells with an optical path of 1 cm specifically modified with a rotaflow stopcock, to allow the charging of the solution in an inert atmosphere and also to ensure a better seal and consequently minimize degradation phenomena by oxidation and/or hydrolysis.

Characterization of the Polymers and Copolymers

The content of monomeric units deriving from 1-hexene in the ethylene-1-hexene copolymers was determined according to the standard technique ASTM D6645-01.

The Melt Flow Index (MFI), correlated to the weight average molecular weight of the polymer, was determined according to the standard technique ASTM-D1238-10. The following tables indicate the Melt Flow Index (MFI) measured with a weight of 2.16 kg at 190° C., expressed as grams of molten polymer in 10 minutes (g/10 min).

The density (g/cm$^3$) was determined according to the standard technique ASTM D2839-10.

Example 1

Synthesis of $Zr(\eta^6\text{-benzene})_2(Al_3Cl_{11})$

A suspension of aluminium in powder form (5.06 g, 187.5 mmoles) in benzene (430 ml) was treated with fresh sublimed $AlCl_3$ (8.60 g, 64.5 mmoles) and $ZrCl_4$ (7.16 g, 30.7 mmoles). The mixture was left at reflux temperature (120° C.) for 24 hours. With the passing of time, the suspension slowly changed colour, from yellow to pink and finally became a dark purple colour. The suspension was filtered under heat, on a G3 filter, and the solid was separated (4.3 g). From ICP elemental analysis, said solid proved to have the following metal content (weight %): Al 82.4%, Zr 2.6%, whereas the Cl content, determined by means of potentiometric titration, was equal to 8.9%. After separation of the solid, the volume of the solution was reduced to about 100 ml by evaporation of the solvent under vacuum. 150 ml of anhydrous n-heptane were added to the residue and the mixture was left under vigorous stirring for about 1 hour and then placed in a refrigerator at about 4° C., for 24 hours. The dark precipitated solid was recovered by rapid filtration of the cold suspension, washed with benzene and dried under vacuum obtaining 10.5 g. From elemental analysis by means of ICP, said solid proved to have the following metal content (weight %): Zr 11.7%, Al 12.8%, whereas the Cl content, determined by means of potentiometric titration, was equal to 55%.

The remaining 20.5% by weight of the above solid substantially consists of organic residue and a minimum part (<0.5% by weight) of impurities, whose nature was not further determined, either in the present example or in the subsequent examples.

UV-Vis analysis (benzene) revealed the following three bands: at 366 nm (weak), at 416 nm (intense), at 492 nm (weak).

Example 2

Synthesis of $Zr(\text{benzene})Al_2Cl_6(\text{n-octyl})_2$ and Isolation of the Solid Component A suspension of $ZrCl_4$ (527 mg, 2.26 mmoles), Al (92.0 mg, 3.41 mmoles), $AlCl_3$ (905 mg, 6.79 mmoles) in a benzene/mesitylene mixture (40/10 ml) was heated to reflux temperature for 3 hours. The system was treated with Al(octyl)$_3$ (10.0 ml of solution in n-hexane at 25% w/w, 4.78 mmoles). The solution obtained was filtered on a porous septum to eliminate the aluminium metal in excess. The volume of the solvent was reduced by evaporation at reduced pressure and 20 ml of cold n-pentane were added. The suspension was left under stirring for 60 hours at about 10° C., the solvent was then removed by evaporation under vacuum. The addition of cold n-pentane was repeated a second time and, after filtration of the precipitate obtained, 640 mg (43%) of a dark brown solid were isolated. Elemental analysis, chlorine, carbon and hydrogen determination carried out on the solid gave the following elemental atomic ratios: $C_{22}H_{40}ZrAl_2Cl_6$.

The determination of the carbon and hydrogen was carried out by means of a Carlo Erba automatic analyzer Mod. 1106.

UV-Vis analysis (dichloroethane) gave the following result: weak band at 524 nm.

The solid was also characterized by means of an IR spectrum (nujol) showing the following bands: 3083 m, 1525 m, 1324 m, 1157 m, 999 vw, 884 m, 880 vw, 788 m, 706 m, 674 w, 550 m, 507 w, 494 w, 438 m, 386 m, 320 w.

Example 3

Preparation of a Solution Containing Zr(mesitylene)-Al$_2$Cl$_6$(n-octyl)$_2$

A suspension of ZrCl$_4$ (527 mg, 2.26 mmoles), Al (92.0 mg, 3.41 mmoles), AlCl$_3$ (905 mg, 6.79 mmoles) in mesitylene (40 ml), was heated to reflux temperature for 3 hours. The system was treated with Al(octyl)$_3$ (10.0 ml of solution in n-hexane at 25% w/w, 4.78 mmoles). The solution obtained was filtered on a porous septum to eliminate the aluminium metal in excess. After filtration, the solution obtained (reaction raw product) can be used as such in the preparation of the solid catalyst component object of the present invention.

UV-Vis analysis (benzene/mesitylene: 4/1) gave the following result: two intense bands at 370 nm and 540 nm.

Example 4

Reaction Between Zr($\eta^6$-benzene)$_2$(Al$_3$Cl$_{11}$) Obtained in Example 1 and TiCl$_4$ in a Molar Ratio 1:1 (SYNZrTi1)

A solution of Zr($\eta^6$-benzene)$_2$(Al$_3$Cl$_{11}$) (0.99 mmoles) obtained as described in Example 1 in 30 ml of benzene, was treated with TiCl$_4$ (0.99 mmoles): the rapid formation of a brown solid was observed. After 3 hours of stirring at room temperature and 30 minutes at 60° C., the suspension was filtered, the solid was washed with benzene and dried under vacuum at room temperature obtaining 0.5 g of a solid. Elemental analysis and chlorine determination carried out on the solid obtained gave the following elemental atomic ratios: Zr$_{1.38}$TiAl$_{0.75}$Cl$_{10.7}$ (SYNZrTi1).

Example 5

Reaction Between Zr($\eta^6$-benzene)$_2$(Al$_3$Cl$_{11}$) Obtained in Example 1 and TiCl$_4$ in a Molar Ratio 1:2 (SYNZrTi2)

A solution of Zr($\eta^6$-benzene)$_2$(Al$_3$Cl$_{11}$) obtained as described in Example 1 (1.10 mmoles) in 30 ml of benzene, was treated with TiCl$_4$ (2.21 mmoles): the rapid formation of a brown solid was observed. After 3 hours of stirring at room temperature and 30 minutes at 60° C., the suspension was filtered, the solid was washed with benzene and dried under vacuum at room temperature obtaining 0.89 g of a solid. Elemental analysis and chlorine determination carried out on the solid obtained gave the following elemental atomic ratios: Zr$_{0.55}$Ti$_1$Al$_{1.21}$Cl$_9$ (SYNZrTi2).

Example 6

Reaction Between Zr($\eta^6$-benzene)$_2$(Al$_3$Cl$_{10}$ Obtained in Example 1 and VCl$_4$ in a Molar Ratio 1:1

A solution of Zr($\eta^6$-benzene)$_2$(Al$_3$Cl$_{11}$) obtained as described in Example 1 (1.20 mmoles) in 30 ml of benzene, was treated with VCl$_4$ (1.20 mmoles). The suspension was left under stirring at room temperature for 15 hours and heated to reflux temperature for 5 hours. The solid obtained was filtered and dried at room temperature at reduced pressure obtaining 0.82 g of a solid. Elemental analysis and chlorine determination carried out on the solid obtained gave the following elemental atomic ratios: ZrVAl$_{3.1}$Cl$_{13.9}$.

Example 7

Reaction Between Zr($\eta^6$-benzene)$_2$(Al$_3$Cl$_{11}$) Obtained in Example 1 and TiCl$_4$ (Molar Ratio Ti/Zr=2:1) in the Presence of MgCl$_2$ (Molar Ratio Mg/Ti=5) at 98° C. (SYNZrTi3)

A solution of Zr($\eta^6$-benzene)$_2$(Al$_3$Cl$_{11}$) obtained as described in Example 1 (0.98 moles) in 30 ml of benzene, was slowly added dropwise into a suspension of TiCl$_4$ (1.96 mmoles) in n-heptane (90 ml) to which anhydrous MgCl$_2$ (9.8 mmoles) had been added. The suspension was heated to reflux temperature for 6 hours obtaining a brown solid which was recovered by filtration, washed with n-heptane and dried under vacuum at room temperature. 1.7 g of a solid were obtained. Elemental analysis and chlorine determination carried out on the solid obtained gave the following elemental atomic ratios: Ti$_1$Zr$_{0.58}$Al$_{1.5}$Mg$_{4.8}$Cl$_{19}$ (SYNZrTi3).

Example 8

Reaction Between Zr($\eta^6$-benzene)$_2$(Al$_3$Cl$_{11}$) Obtained in Example 1 and TiCl$_4$ (Molar Ratio Ti/Zr=1:1) in the Presence of MgCl$_2$(THF)$_2$ (Molar Ratio Mg/Ti 10), tert-butylchloride at 98° C. (SYNZrTi4)

A solution of Zr($\eta^6$-benzene)$_2$(Al$_3$Cl$_{11}$) obtained as described in Example 1 (2.79 moles) in 30 ml of benzene, was slowly added dropwise into a suspension of TiCl$_4$ (2.79 mmoles) in n-heptane (100 ml) to which MgCl$_2$(THF)$_2$ (27.9 mmoles) had been added. After leaving the suspension under stirring for 1 hour, a solution of tert-butylchloride (16.8 mmoles) was added. The suspension was then heated to reflux temperature for 6 hours obtaining a brown solid which was recovered by filtration, washed with n-heptane and dried under vacuum at room temperature. 3.6 g of a solid were obtained. Elemental analysis and chlorine determination carried out on the solid obtained gave the following elemental atomic ratios: Ti$_1$Zr$_1$Al$_{3.1}$Mg$_9$Cl$_{27}$ (SYNZrTi4).

Example 9

Reaction Between Zr($\eta^6$-benzene)$_2$(Al$_3$Cl$_{11}$) Obtained in Example 1 and TiCl$_4$ (Molar Ratio Ti/Zr=3:1) in the Presence of (n-C$_4$H$_9$)$_{1.5}$(n-C$_8$H$_{17}$)$_{0.5}$Mg (Molar Ratio Mg/Ti=1) and 2,3-dichlorobutane at 60° C. (SYNZrTi5)

A solution in n-heptane (20% w/w) of (n-C$_4$H$_9$)$_{1.5}$(n-C$_8$H$_{17}$)$_{0.5}$Mg (2.3 mmoles) was added to a solution of Zr($\eta^6$-benzene)$_2$(Al$_3$Cl$_{11}$) obtained as described in Example 1 (2.3 mmoles) in 30 ml of benzene, and a solution of TiCl$_4$ (6.9 mmoles) in n-heptane (35 ml) was slowly added dropwise. After leaving the suspension under stirring for 30 minutes, a solution of 2,3-dichlorobutane (2.3 mmoles) was added. The suspension was then heated to 60° C. for 1 hour obtaining a brown solid which was recovered by filtration, washed with n-heptane and dried under vacuum at room temperature. 2.1 g of a solid were obtained. Elemental analysis and chlorine determination carried out on the solid obtained gave the following elemental atomic ratios: Ti$_1$Zr$_{0.4}$Al$_{0.6}$Mg$_{0.4}$Cl$_7$ (SYNZrTi5)

Example 10

Reaction Between a Solution Containing Zr(mesity-lene)-Al$_2$Cl$_6$(n-octyl) and TiCl$_4$ (Molar Ratio Ti/Zr=2) (SYNZrTi6)

A suspension of ZrCl$_4$ (323 mg, 1.39 moles), Al (56 mg, 2.08 mmoles), AlCl$_3$ (555 mg, 4.16 mmoles) in mesitylene (40 ml), was heated to 160° C., for 3 hours. The system was treated with Al(octyl)$_3$ (5.1 ml of solution in n-hexane at 25% w/w, 2.60 mmoles). The solution obtained was filtered on a porous septum to eliminate the aluminium metal in excess and was then treated dropwise with TiCl$_4$ (0.38 ml, 2.81 mmoles) in a solution of n-heptane (20 ml). At the end of the addition, the brown suspension was left under stirring, at room temperature, for 15 hours obtaining 1.01 g of a brown solid. Elemental analysis and chlorine determination carried out on the solid obtained gave the following elemental atomic ratios: Ti$_1$Zr$_{0.5}$Al$_2$Cl$_{14}$ (SYNZrTi6).

Example 11

Reaction Between a Solution Containing Zr(mesity-lene)-Al$_2$Cl$_6$(n-octyl)$_2$ and TiCl$_4$ (Molar Ratio Ti/Zr=1.3) in the Presence of MgCl$_2$(THF)$_2$ (Molar Ratio Mg/Ti=3.4) at Room Temperature (SYNZrTi7)

A suspension of ZrCl$_4$ (380 mg, 1.63 mmoles), Al (66.0 mg, 2.45 mmoles), AlCl$_3$ (652 mg, 4.89 mmoles) in mesitylene (40 ml), was heated to 160° C., for 3 hours. The system was treated with Al(octyl)$_3$ (5.1 ml of solution in n-hexane at 25% w/w, 2.44 mmoles). The solution obtained was filtered on a porous septum to eliminate the aluminium metal in excess. After treatment with solid MgCl$_2$(THF)$_2$ (2.82 g, 11.8 mmoles), the resulting suspension was treated dropwise with TiCl$_4$ (0.38 ml, 3.47 mmoles) in a solution of n-heptane (20 ml). At the end of the addition, the suspension was left under stirring, at room temperature, for 15 hours obtaining 3.82 g of a greyish-green solid. Elemental analysis and chlorine determination carried out on the solid obtained gave the following elemental atomic ratios: Ti$_1$Zr$_{0.5}$Al$_{0.7}$Mg$_{4.14}$Cl$_{14.7}$ (SYNZrTi7).

Example 12

Reaction Between a Solution Containing Zr(mesity-lene)-Al$_2$Cl$_6$(n-octyl)$_2$ and TiCl$_4$ (Molar Ratio Ti/Zr=2) in the Presence of MgCl$_2$(THF)$_2$ (Molar Ratio Mg/Ti=3) at 120° C. (SYNZrTi8)

A suspension of ZrCl$_4$ (223 mg, 0.96 mmoles), Al (39.0 mg, 1.44 mmoles), AlCl$_3$ (383 mg, 2.87 mmoles) in mesitylene (40 ml), was heated to 160° C., for 3 hours. The system was treated with Al(octyl)$_3$ (3.0 ml of solution in n-hexane at 25% w/w, 1.43 mmoles). The solution obtained was filtered on a porous septum to eliminate the aluminium metal in excess. After treatment with solid MgCl$_2$(THF)$_2$ (1.48 g, 6.18 mmoles), the resulting suspension was treated dropwise with TiCl$_4$ (0.22 mL, 2.01 mmoles) in a solution of n-heptane (20 ml). At the end of the addition, the suspension was heated to 120° C., for 8 hours, obtaining 4.50 g of a grey solid. Elemental analysis and chlorine determination carried out on the solid obtained gave the following elemental atomic ratios: Ti$_1$Zr$_{0.5}$Mg$_4$Al$_1$Cl$_{10}$ (SYNZrTi8).

Example 13

Reaction Between a Solution Containing Zr(mesity-lene)-Al$_2$Cl$_6$(n-octyl)$_x$ and TiCl$_4$ (Molar Ratio Ti/Zr=1) in the Presence of MgCl$_2$(DME)$_2$ (Molar Ratio Mg/Ti=9) and 2,3-dichlorobutane (DCB/Zr=40) at 120° C. (SYNZrTi9)

A suspension of ZrCl$_4$ (229 mg, 0.983 mmoles), Al (40 mg, 1.48 mmoles), AlCl$_3$ (400 mg, 3.00 mmoles) in mesitylene (40 ml), was heated to 160° C., for 3 hours. The system was treated with Al(octyl)$_3$ (3.1 ml of solution in n-hexane at 25% w/w, 1.48 moles). The solution obtained was filtered on a porous septum to eliminate the aluminium metal in excess. After treatment with MgCl$_2$(DME)$_2$ (5.01 g, 18.2 mmoles), the resulting suspension was treated dropwise in order, with TiCl$_4$ (0.22 ml, 2.01 mmoles) in a solution of n-heptane (10.0 ml) and 2,3-dichlorobutane (4.5 ml, 39.3 mmoles). At the end of the addition, the suspension was heated to 120° C., for 15 hours, obtaining 4.25 g of a grey solid having a homogeneous appearance. Elemental analysis and chlorine determination carried out on the solid obtained gave the following elemental atomic ratios: Ti$_1$Zr$_{0.3}$Mg$_{7.7}$Al$_{1.9}$Cl$_{20.5}$ (SYNZrTi9).

Example 14

Reaction Between a Solution Containing Zr(mesity-lene)-Al$_2$Cl$_6$(n-octyl)$_2$ and TiCl$_4$ (Molar Ratio Ti/Zr=1) in the Presence of MgCl$_2$(THF)$_2$ (Molar Ratio Mg/Ti=10) and 2,3-dichlorobutane (DCB/Zr=20) at 120° C. (SYNZrTi10)

A suspension of ZrCl$_4$ (396 mg, 1.70 mmoles), Al (69.0 mg, 2.56 mmoles), AlCl$_3$ (680 mg, 5.10 mmoles) in mesitylene (40 ml), was heated to 160° C., for 3 hours. The system was treated with Al(octyl)$_3$ (7.1 ml of solution in n-hexane at 25% w/w, 3.40 mmoles). The solution obtained was filtered on a porous septum to eliminate the aluminium metal in excess. After treatment with MgCl$_2$(THF)$_2$ (4.06 g, 16.9 mmoles), the resulting suspension was treated dropwise in order, with TiCl$_4$ (0.19 ml, 1.70 mmoles) in a solution of n-heptane (10.0 ml) and 2,3-dichlorobutane (4.0 ml, 34.9 mmoles). At the end of the addition, the suspension was heated to 120° C., for 15 hours, obtaining 3.74 g of a grey solid having a homogeneous appearance. Elemental analysis and chlorine determination carried out on the solid obtained gave the following elemental atomic ratios: Ti$_1$Zr$_1$Mg$_{11.4}$Al$_{1.6}$Cl$_{32.3}$ (SYNZrTi10).

Example 15

Reaction of the Solid Catalyst Component Obtained in Example 10 with MgCl$_2$(THF)$_2$ (Molar Ratio Mg/Ti=10) in n-heptane at Reflux Temperature (SYNZrTi11)

A suspension of MgCl$_2$(THF)$_2$ (1.48 g, 6.18 moles) in n-heptane (50 ml) was treated with a sample of the solid catalyst component obtained as described in Example 10, having a titanium content equal to 10.0% (30.5 mg of Ti, 0.637 mmoles). The suspension was heated to the reflux temperature of the solvent, for 15 hours, obtaining 1.10 g of a grey solid having a homogeneous appearance. Elemental analysis and chlorine determination carried out on the solid obtained gave the following elemental atomic ratios: Ti$_1$Zr$_1$Mg$_{10.6}$Al$_{1.2}$Cl$_{26}$ (SYNZrTi11).

Example 16

(Co)Polymerization Tests with the Solid Catalyst Components SYNZrTi1-SYNZrTi5

The tests reported in Table 1 (Tests 1-2), Table 2 (Tests 3-4) and Table 3 (Tests 5-9), were carried out in a Büchi steel autoclave having a volume of 300 ml, equipped with a propeller stirrer and double jacket for thermostat heating. A vacuum-nitrogen flushing was exerted in the autoclave for at least three times and said autoclave was left under vacuum at 100° C.-110° C., for an overall duration of about 2 hours. The autoclave was then cooled to 40° C. and a solution containing 140 ml of n-heptane (130 ml of n-heptane and 10 ml of 1-hexene, in the case of copolymerization) and 0.2 ml (0.75 mmoles) of TIBAL as co-catalyst, was charged, by siphoning through a valve. The temperature inside the autoclave was brought to 65° C. and at that point, a solution containing 10 ml of n-heptane, 0.2 ml (0.75 mmoles) of TIBAL (solution in toluene at 23% w/w) and the solid catalyst component (SYNZrTi1-SYNZrTi5) (Ti=0.015 mmoles) (molar ratio Al/Ti=100), was introduced, again by siphoning. The autoclave was subsequently pressurized with ethylene (0.6 MPa), heated to 80° C., and the whole mixture was left to polymerize at 80° C., for 10 minutes, in a continuous flow of ethylene. The ethylene feeding was then closed, the autoclave was cooled to room temperature, the residual gases were vented and the suspension contained in the autoclave was discharged and poured into ethanol. The polymer was recovered by filtration and dried under vacuum, at 60° C., for a few hours.

Example 17

Polymerization Tests with the Solid Catalyst Components SYNZrTi6, SYNZrTi7, SYNZrTi10, SYNZrTi11

The tests reported in Table 4 (Tests 10-13) were carried out in a steel autoclave having a volume of 150 ml equipped with magnetic stirring and optionally heated in a thermostat-regulated oil bath. The solid catalyst component (SYNZrTi6, SYNZrTi7, SYNZrTi10 and SYNZrTi11) was suspended in 60 ml of n-heptane, a quantity of a solution of TIBAL in toluene at 25% w/w was then added so as to obtain a molar ratio Al/Ti=100, and the resulting mixture was transferred to the autoclave. The autoclave was subsequently pressurized with ethylene (1 MPa) and introduced into the oil bath thermostat-regulated at the desired reaction temperature (80° C.). At the end of the reaction (15 minutes), the ethylene feeding was closed, the autoclave was cooled to room temperature, the residual gases were vented and the suspension contained in the autoclave was discharged and poured into acidified methanol. The polymer precipitated was washed with methanol, filtered and dried under vacuum, at 60° C., for a few hours.

Example 18

Polymerization of Ethylene with the Solid Catalyst Component Obtained in Example 11(SYNZrTi7)

A vacuum-nitrogen flushing was exerted for at least three times and for an overall duration of about 2 hours in a 5-liter steel autoclave, of the Brignole type, equipped with a burette for the addition of the catalyst, a propeller stirrer and a heating thermoresistance connected to a thermostat for the temperature control. A solution containing 1,900 ml of n-decane, 1.5 ml of a 1 M solution of TIBAL (1.5 mmoles) in n-decane as cocatalyst (molar ratio Al/Ti=23), was then introduced into the autoclave. The temperature inside the autoclave was brought to 190° C., and 86 mg of the solid catalyst component obtained as described in Example 11 (SYNZrTi7) (65 µmoles of Ti), was introduced by means of a burette, under a slight overpressure of ethylene, as a suspension in about 10 ml of n-decane. The autoclave was pressurized with ethylene, keeping under stirring, until a total pressure was reached in the autoclave equal to 1.5 MPa. At this point, the heating of the thermoresistance was interrupted and a temperature increase due to the exothermicity of the polymerization reaction, was observed. The entity of the enthalpy variation ($\Delta$H) can be directly correlated to the activity of the ethylene converted and proportional to the catalytic activity obtained. The ethylene flow necessary for replacing the ethylene converted into polymer, was also registered by means of ASA flow-meters calibrated with an analog volume meter. The polymerization was continued for 5 minutes, maintaining the system at a constant pressure of 1.5 MPa. At the end, the polymerization reaction was interrupted by the introduction of about 10 ml of ethanol into the autoclave. The autoclave was left to cool to room temperature and, subsequently, the contents of the autoclave was discharged into about 3 liters of ethanol. The polymer was separated by filtration, washed with acetone and dried in an oven under vacuum (about 100 Pa), at 90° C., for about hours. At the end, 37 g of polyethylene homopolymer were obtained, which was characterized by measuring the Melt Flow Index (MFI) and the density: the results obtained are reported in Table 5.

Example 19

Polymerization of Ethylene with the Solid Catalyst Component Obtained in Example 11 (SYNZrTi7) Using a 1:1 Mixture of TIBAL and DEAC, as Co-Catalyst The same procedure was used as described in Example 18, with the difference that 1.5 ml of a mixture of a solution 1 M of TIBAL and 1 M of DEAC with a molar ratio 1:1 (1.5 mmoles) in n-decane as co-catalyst (molar ratio Al/Ti=28.7), were charged into the autoclave.

The autoclave was heated to a temperature of 160° C., 69.6 mg of the solid catalyst component obtained as described in Example 11 (SYNZrTi7) (52.2 µmoles Ti), were added, as a suspension in about 15 ml of n-decane, and the polymerization reaction was carried out with the same procedure described above in Example 18, for a time of 10 minutes. At the end, the polymer obtained was recovered and treated analogously to what is described above in Example 18. 48 g of polyethylene homopolymer were obtained, which was characterized by measuring the Melt Flow Index (MFI) and the density: the results obtained are reported in Table 6.

Example 20

Polymerization of Ethylene with the Solid Catalyst Component Obtained in Example 12 (SYNZrTi8)

The same procedure was used as described in Example 18, with the difference that 1.5 ml of a solution 1 M of TIBAL (1.5 mmoles) in n-decane as co-catalyst (molar ratio Al/Ti=30) and, at a starting temperature of 190° C., 41.1 mg of the solid catalyst component obtained as described in Example 12 (SYNZrTi8) (50 µmoles Ti), as a suspension in about 15 ml of n-decane, were charged into the autoclave. The polymerization reaction was carried out with the same procedure described above in Example 18, for a time of 5 minutes. At the end, the polymer obtained was recovered and treated analogously to what is described above in Example 18. 28 g of polyethylene homopolymer were obtained, which was characterized by measuring the Melt Flow Index MFI) and the density: the results obtained are reported in Table 5.

Example 21

Polymerization of Ethylene with the Solid Catalyst Component Obtained in Example 14 (SYNZrTi10)

The same procedure was used as described in Example 18, with the difference that 1.5 ml of a solution 1 M of TIBAL (1.5 mmoles) in n-decane as co-catalyst (molar ratio Al/Ti=30 and, at a starting temperature of 190° C., 73.2 mg of the solid catalyst component obtained as described in Example 14 (SYNZrTi10) (50 μmoles Ti), as a suspension in about 15 ml of n-decane), were charged into the autoclave. The polymerization reaction was carried out with the same procedure described above in Example 18, for a time of 5 minutes. At the end, the polymer obtained was recovered and treated analogously to what is described above in Example 18. 20 g of polyethylene homopolymer were obtained, which was characterized by measuring the Melt Flow Index (MFI) and the density: the results obtained are reported in Table 5.

Example 22

Polymerization of Ethylene with the Solid Catalyst Component Obtained in Example 14 (SYNZrTi10)

The same procedure was used as described in Example 18, with the difference that 1.5 ml of a solution 1 M of TIBAL (1.5 mmoles) in n-decane as co-catalyst (molar ratio Al/Ti=30), were charged into the autoclave. The autoclave was heated to 160° C. and 73.2 mg of the solid catalyst component obtained as described in Example 14 (SYNZrTi10) (50 μmoles Ti), were added as a suspension in about 15 ml of n-decane. The polymerization reaction was carried out with the same procedure described above in Example 18, for a time of 5 minutes. At the end, the polymer obtained was recovered and treated analogously to what is described above in Example 18. 40 g of polyethylene homopolymer were obtained, which was characterized by measuring the Melt Flow Index (MFI) and the density: the results obtained are reported in Table 6.

Example 23

Polymerization of Ethylene with the Solid Catalyst Component Obtained in Example 14 (SYNZrTi10) Using a 1:1 Mixture of TIBAL and DEAC, as Co-Catalyst The same procedure was used as described in Example 18, with the difference that 1.5 ml of a mixture of a solution 1 M of TIBAL and 1 M of DEAC with a molar ratio 1:1 (1.5 moles) in n-decane as co-catalyst (molar ratio Al/Ti=37.5), were charged into the autoclave. The autoclave was heated to a temperature of 160° C., 58.5 mg of the solid catalyst component obtained as described in Example 14 (SYNZrTi10) (40 μmoles Ti), were added as a suspension in about 15 ml of n-decane, and the polymerization reaction was carried out with the same procedure described above in Example 18, for a time of 10 minutes. At the end, the polymer obtained was recovered and treated analogously to what is described above in Example 18. 50 g of polyethylene homopolymer were obtained, which was characterized by measuring the Melt Flow Index (MFI) and the density: the results obtained are reported in Table 6.

Example 24

Polymerization of Ethylene with the Solid Catalyst Component Obtained in Example 14 (SYNZrTi10) Treated with DEAC in a Ratio Al(DEAC)/Ti=20

278 mg of solid catalyst component obtained as described in Example 14 (SYNZrTi10) (containing 4.79 mg of titanium=0.1 mmoles) and 15 ml of n-decane, were introduced under nitrogen flow, into a 100 ml glass tailed test-tube. 20 ml of a solution 1 M of DEAC in n-decane were subsequently added, under stirring at room temperature, so as to have a molar ratio Al(DEAC)/Ti=20 (Al/Ti=20). The whole mixture was left under stirring, for 60 minutes, at room temperature, obtaining 265 mg of a solid which was filtered, washed with n-decane and dried.

Elemental analysis and chlorine determination carried out on the solid obtained gave the following elemental atomic ratios: $Ti_1Zr_1Mg_{11.4}Al_{1.6}Cl_{32.1}$ (SYNZrTi10). Said solid was resuspended with about 10 ml of n-decane and kept in suspension for the subsequent polymerization test.

As can be observed from the atomic ratios obtained, the treatment with DEAC does not significantly modify the composition of the solid catalyst component obtained as described in Example 14, even if its activity is considerably increased. This behaviour was observed systematically during various laboratory tests and consequently, in the following examples, the composition of the solid catalyst components thus prepared is considered the same as the solid catalyst components obtained without treatment with DEAC, without proceeding each time with elemental analysis.

The subsequent polymerization reaction was carried out using the same procedure described in Example 18, with the difference that 1.5 ml of a solution 1 M of TI-BAL (1.5 mmoles) in n-decane (molar ratio Al/Ti=30 and, at a starting temperature of 190° C., 111.4 mg of the solid catalyst component prepared as described above (40 μmoles Ti), as a suspension in about 15 ml of n-decane), were charged into the autoclave. The polymerization reaction was carried out with the same procedure described above in Example 18, for a time of 5 minutes. At the end, the polymer obtained was recovered and treated analogously to what is described above in Example 18. 40 g of polyethylene homopolymer were obtained, which was characterized by measuring the Melt Flow Index (MFI) and the density: the results obtained are reported in Table V.

Example 25

Polymerization of Ethylene with the Solid Catalyst Component Obtained in Example 14 (SYNZrTi10) Treated with DEAC in a Ratio Al(DEAC)/Ti=20

The same procedure was adopted as described in Example 24 with the only difference that, after the addition of DEAC at room temperature, the preformed suspension was heated to 60° C. for 60 minutes, before being filtered. As in the previous Example 24, the treatment did not produce any significant variations in the chemical composition of the solid catalyst component obtained as described in Example 14 (SYNZrTi10).

The subsequent polymerization reaction was carried out according to the procedure described in Example 24, but with the addition, however, of 75 g of 1-hexene, together with n-decane.

1.5 ml of a solution 1 M of TIBAL (1.5 mmoles) in n-decane as co-catalyst (molar ratio Al/Ti=30) and, at a starting temperature of 190° C., 111.4 mg of the solid catalyst component prepared as described above (40 μmoles Ti), as a suspension in about 15 ml of n-decane, were charged into the autoclave. The polymerization reaction was carried out with the same procedure described above in Example 18, for a time of 5 minutes. At the end, the polymer obtained was recovered and treated analogously to what is described above in Example 18. 55 g of copolymer were obtained, which was characterized by measuring the Melt Flow Index (MFI) and the density: the results obtained are reported in Table 7.

Example 26

Polymerization of Ethylene with the Solid Catalyst Component Obtained in Example 15 (SYNZrTi11)

The same procedure was used as described in Example 18, with the difference that 1.5 ml of a solution 1 M of TIBAL (1.5 mmoles) in n-decane as co-catalyst (molar ratio Al/Ti=30) and, at a starting temperature of 190° C., 102.50 mg of the solid catalyst component obtained as described in Example 15 (SYNZrTi11) (50 μmoles Ti), as a suspension in about 15 ml of n-decane, were charged into the autoclave. The polymerization reaction was carried out with the same procedure described above in Example 18, for a time of 5 minutes. At the end, the polymer obtained was recovered and treated analogously to what is described above in Example 18. 17 g of polyethylene homopolymer were obtained, which was characterized by measuring the Melt Flow Index (MFI) and the density: the results obtained are reported in Table 5.

Example 27

Reaction Between the Biphasic System (Reaction Raw Product) Containing $Zr(\eta^6$-toluene)(AlCl$_4$)$_2$ and TiCl$_4$ in a Molar Ratio 1:2 (SYNZrTi12)

A suspension of ZrCl$_4$ (1.4 g, 6.01 mmoles), aluminium in powder form (1.0 g, 37.1 mmoles) and AlCl$_3$ (1.75 g, 13.2 mmoles) in toluene (100 ml) was heated to reflux temperature, for 24 hours, obtaining a biphasic system (reaction raw product) consisting of an overlying purple-coloured phase and an underlying very dark purple phase, extremely viscous. Said biphasic system was heated to about 100° C. and filtered under heat. The filter and walls of the reaction container were washed with toluene at boiling point. After filtration, the biphasic system was treated with TiCl$_4$ (13 mmoles) and the suspension obtained was heated to 50° C.-60° C. for 15 hours. The brown solid precipitated was recovered by filtration of the suspension, after cooling the same to room temperature, and dried at reduced pressure at room temperature. 3.9 g of a solid were obtained. Elemental analysis and chlorine determination carried out on the solid obtained gave the following elemental atomic ratios: Ti$_2$Zr$_1$Al$_{2.5}$Cl$_{18}$ (SYNZrTi12).

Example 28

Reaction Between the Biphasic System (Reaction Raw Product) Containing $Zr(\eta^6$-toluene)(AlCl$_4$)$_2$ and VCl$_4$ in a Molar Ratio 1:1

A suspension of ZrCl$_4$ (0.70 g, 3.0 mmoles), aluminium in powder form (0.50 g, 18.5 mmoles) and AlCl$_3$ (0.81 g, 6.07 mmoles) in toluene (100 ml) was heated to reflux temperature, for 24 hours, obtaining a biphasic system (reaction raw product) consisting of an overlying purple-coloured phase and an underlying very dark purple phase, extremely viscous. Said biphasic system was heated to about 50° C.-60° C. and filtered under heat. The filter and walls of the reaction container were washed with toluene at boiling point. After filtration, the biphasic system was treated with VCl$_4$ (3.1 mmoles) and the suspension obtained was left under stirring, at room temperature, for 15 hours, and heated to reflux temperature for 5 hours. The solid precipitated was recovered by filtration of the suspension, after cooling the same to room temperature, and dried at reduced pressure at room temperature. 0.82 g of a solid were obtained. Elemental analysis and chlorine determination carried out on the solid obtained gave the following elemental atomic ratios: VZrAl$_{2.2}$Cl$_{11.9}$.

Example 29

Reaction Between the Biphasic System (Reaction Raw Product) Containing $Zr(\eta^6$-toluene)(AlCl$_4$)$_2$ and TiCl$_4$ (Molar Ratio Ti/Zr=16) in the Presence of an Excess of Aluminium (SYNZrTi13)

A suspension of ZrCl$_4$ (0.70 g, 3.0 mmoles), aluminium in powder form (0.30 g, 11.2 mmoles) and AlCl$_3$ (1.31 g, 9.82 mmoles) in toluene (100 ml) was heated to reflux temperature, for 15 hours, obtaining a biphasic system (reaction raw product) consisting of an overlying purple-coloured phase and an underlying very dark purple phase, extremely viscous. Said biphasic system was treated with TiCl$_4$ (48 mmoles) in n-heptane (20 ml) and the mixture obtained was heated to reflux temperature for a whole night. The brown solid precipitated was recovered by filtration of the suspension, after cooling the same to room temperature, and dried at reduced pressure at room temperature. 1.5 g of a brown solid were obtained. Elemental analysis and chlorine determination carried out on the solid obtained gave the following elemental atomic ratios: TiZr$_{0.31}$Al$_{0.46}$Cl$_{5.5}$ (SYNZrTi13).

Example 30

Reaction Between the Biphasic System (Reaction Raw Product) Containing $Zr(\eta^6$-toluene)(AlCl$_4$)$_2$ and TiCl$_4$ (Molar Ratio Zr/Ti=10) in the Presence of an Excess of Aluminium (SYNZrTi14)

The same procedure was adopted as described above in Example 29, with the difference that the biphasic system obtained was treated with TiCl$_4$ (30 mmoles) in n-heptane (20 ml) and the mixture obtained was heated to reflux temperature for a whole night. The brown solid precipitated was recovered by filtration of the suspension, after cooling the same to room temperature, and dried at reduced pressure at room temperature. 0.95 g of a brown solid were obtained. Elemental analysis and chlorine determination carried out on the solid obtained gave the following elemental atomic ratios: TiZr$_{0.12}$Al$_{0.2}$Cl$_4$ (SYNZrTi14). It should be noted that although the analysis clearly shows the presence of non-reacted aluminium, said solid catalyst component proved to be active in the polymerization of ethylene (see Table 9).

Example 31

Polymerization Tests with the Solid Catalyst Components SYNZrTi12-SYNZrTi14

The tests reported in Table 8 (Tests 1-2) and in Table 9 (Tests 3-6) were carried out in a steel autoclave having a volume of 150 ml equipped with magnetic stirring and optionally heated in a thermostat-regulated oil bath. The solid catalyst component (SYNZrTi12, SYNZrTi13 and SYNZrTi14) was suspended in 10 ml of n-heptane, a quantity of a solution of TIBAL in toluene at 25% w/w was then added so as to obtain a molar ratio Al/Ti=100, and the resulting mixture was transferred to the autoclave. The autoclave was subsequently pressurized with ethylene (0.6 MPa in Tests 1-2; 1 MPa in Tests 3-6) and introduced into the oil bath thermostat-regulated at the desired reaction temperature (80° C.). At the end of the reaction (30 minutes in Tests 1-2; 15 minutes in Tests 3-6), the reaction mixture was discharged from the autoclave and poured into acidified methanol, and the polymer precipitated was washed with methanol and filtered.

TABLE 1

Polymerization of ethylene and copolymerization of ethylene with 1-hexene with the solid catalyst component SYNZrTi1

| TEST | CATALYST (μmoles of Ti) | PE (g) | ACTIVITY (kg × g$^{-1}$$_{Ti}$ × h$^{-1}$) | ACTIVITY (kg × mol$^{-1}$$_{Ti}$ × h$^{-1}$) | C6* (mol %) |
|---|---|---|---|---|---|
| 1 | 15 | 4.1 | 34 | 1632 | — |
| 2 | 15 | 6.2 | 52 | 2496 | 5 |

Co-catalyst = TIBAL; Al/Ti = 100; n-heptane = 150 ml; P$_{(ethylene)}$ = 0.6 MPa; 1-hexene (C6) = 10 ml; time = 10 min; T = 80° C.
*Calculated by means of FT-IR analysis

TABLE 2

Polymerization of ethylene and copolymerization of ethylene with 1-hexene with the solid catalyst component SYNZrTi2

| TEST | CATALYST (μmoles of Ti) | PE (g) | ACTIVITY (kg × g$^{-1}$$_{Ti}$ × h$^{-1}$) | ACTIVITY (kg × mol$^{-1}$$_{Ti}$ × h$^{-1}$) | C6* (mol %) |
|---|---|---|---|---|---|
| 3 | 15 | 8.6 | 72 | 3456 | — |
| 4 | 15 | 10.6 | 88 | 4224 | 2.8 |

Co-catalyst = TIBAL; Al/Ti = 100; n-heptane = 150 ml; P$_{(ethylene)}$ = 0.6 MPa; 1-hexene (C6) = 10 ml; time = 10 min; T = 80° C.
*Calculated by means of FT-IR analysis

TABLE 3

Polymerization of ethylene and copolymerization of ethylene with 1-hexene with the solid catalyst component SYNZrTi3, SYNZrTi4 and SYNZrTi5.

| TEST | CATALYST (μmoles of Ti) | PE (g) | ACTIVITY (kg × g$^{-1}$$_{Ti}$ × h$^{-1}$) | ACTIVITY (kg × mol$^{-1}$$_{Ti}$ × h$^{-1}$) | C6* (mol %) |
|---|---|---|---|---|---|
| 5 | 14 (SYNZrTi3) | 14 | 125 | 6000 | — |
| 6 | 11 (SYNZrTi4) | 11.9 | 135 | 6480 | — |
| 7 | 15 (SYNZrTi4) | 12.8 | 107 | 5136 | 12.5 |
| 8 | 13 (SYNZrTi5) | 6 | 96 | 4608 | — |
| 9 | 15 (SYNZrTi5) | 10 | 84 | 4032 | 5.8 |

Co-catalyst = TIBAL; Al/Ti = 100; n-heptane = 150 ml; P$_{(ethylene)}$ = 0.6 MPa; 1-hexene (C6) = 10 ml; time = 10 min; T = 80° C.
*Calculated by means of FT-IR analysis

TABLE 4

Polymerization of ethylene with the solid catalyst component SYNZrTi6, SYNZrTi7, SYNZrTi10 and SYNZrTi11.

| TEST | CATALYST (μmoles of Ti) | PE (g) | ACTIVITY (kg × mol$^{-1}$$_{Ti}$ × h$^{-1}$) |
|---|---|---|---|
| 10 | 28.3 (SYNZrTi6) | 9.5 | 1343 |
| 11 | 9.4 (SYNZrTi7) | 7.73 | 3303 |
| 12 | 15.8 (SYNZrTi10) | 8.3 | 2101 |
| 13 | 9.3 (SYNZrTi11) | 4.85 | 2086 |

Co-catalyst = solution of tri-iso-butyl-aluminium (TIBAL) in toluene at 25% w/w; Al/Ti = 100; n-heptane = 60 ml; P$_{(ethylene)}$ = 1 MPa; time = 15 min; T = 80° C.

TABLE 5

Polymerization of ethylene with the solid catalyst components obtained in Examples 11, 12, 14 and 15.

| Example | Catalyst | Ti (mg) | Al/Ti (molar) | Yield (g) | Activity (kg/g$_{Ti}$) | MFI$_{(2,16 kg)}$ (g/10 min) | Density (g/cm$^3$) |
|---|---|---|---|---|---|---|---|
| 18 | SYNZrTi7 | 2.5 | 23 | 37 | 14.8 | 0.124 | 0.9305 |
| 20 | SYNZrTi8 | 2.4 | 30 | 28 | 11.7 | 0.048 | 0.9299 |
| 21 | SYNZrTi10 | 2.4 | 30 | 20 | 8.3 | 0.072 | 0.9304 |
| 26 | SYNZrTi11 | 2.4 | 30 | 17 | 7.1 | 0.024 | 0.9309 |

Co-catalyst = TIBAL; P$_{(ethylene)}$ = 1.5 MPa; Time = 5 min; T initial = 190° C.

TABLE 6

Polymerization of ethylene with the solid catalyst components obtained in Examples 11 and 14

| Example | Catalyst | Ti (mg) | Al/Ti (molar) | Yield (g) | Activity (kg/$g_{Ti}$) | MFI$_{(2.16 kg)}$ (g/10 min) | Density (g/cm$^3$) |
|---|---|---|---|---|---|---|---|
| 19[(1)] | SYNZrTi7  | 3.11 | 29   | 48 | 15.4 | 0.69 | 0.9289 |
| 22[(2)] | SYNZrTi10 | 2.4  | 30   | 40 | 16.6 | 0.79 | 0.9278 |
| 23[(3)] | SYNZrTi10 | 1.92 | 37.5 | 50 | 26   | 0.98 | 0.9276 |

P$_{(ethylene)}$ = 1.5 MPa; time = 5 min; T initial = 160° C.
[(1)] and [(3)] co-catalyst = TIBAL/DEAC
[(2)] co-catalyst = TIBAL

TABLE 7

Ethylene polymerization and ethylene copolymerization with 1-hexene with a catalyst solid component treated with DEAC (Al/Ti = 20)

| Example | Catalyst | Ti (mg) | 1-hexene (g) | Al/Ti (molar) | Yield (g) | Activity (kg/$g_{Ti}$) | MFI$_{(2.16 kg)}$ (g/10 min) | Density (g/cm$^3$) |
|---|---|---|---|---|---|---|---|---|
| 24 | SYNZrTi10 | 1.92 | —  | 30 | 40 | 20.8 | 0.17 | 0.9363 |
| 25 | SYNZrTi10 | 1.92 | 75 | 30 | 40 | 28.6 | 0.10 | 0.9223 |

T initial = 190° C.; [(2)]: co-catalyst = TIBAL; P$_{(ethylene)}$ = 1.5 MPa; t = 5 min

TABLE 8

Polymerization of ethylene with the catalyst solid component SYNZrTi12

| Test | Catalyst (mg) | Ti (µmol) | Al/Ti (molar) | T (° C.) | PE (g) | Activity (kg × mol$^{-1}_{Ti}$ × h$^{-1}$) |
|---|---|---|---|---|---|---|
| 1 | 7   | 6.28 | 50 | 80 | 1.11 | 353 |
| 2 | 5.2 | 12.9 | 50 | 80 | 4.95 | 767 |

Co-catalyst = solution of tri-iso-butyl-aluminium (TIBAL) in toluene at 25% w/w; n-heptane = 60 ml; P$_{(ethylene)}$ = 0.6 MPa; t = 30 min; T = 80° C.

TABLE 9

Polymerization of ethylene with the catalyst solid components SYNZrTi13 and SYNZrTi14

| Test | Catalyst (mg) | Ti (µmol) | Al/Ti (molar) | T (° C.) | PE (g) | Activity (kg × mol$^{-1}_{Ti}$ × h$^{-1}$) |
|---|---|---|---|---|---|---|
| 3 | 12.2 (SYNZrTi13) | 14.8 | 100 | 80 | 3.26 | 828.8 |
| 4 | 16 (SYNZrTi13)   | 19.3 | 50  | 80 | 2.96 | 613.5 |
| 5 | 10 (SYNZrTi14)   | 35.3 | 50  | 80 | 2.3  | 130 |
| 6 | 6 (SYNZrTi14)    | 21.1 | 50  | 80 | 2.73 | 259 |

Co-catalyst = solution of tri-iso-butyl-aluminium (TIBAL) in toluene at 25% w/w; n-heptane = 60 ml; P$_{(ethylene)}$ = 1 MPa; t = 15 min; T = 80° C.

The invention claimed is:

1. A solid catalyst component for the (co)polymerization of α-olefins, the solid catalyst component having general formula (I):

$$Zr_nMAl_xCl_yMg_p \qquad (I)$$

wherein:
M represents titanium (Ti);
n is a number ranging from 0.01 to 2;
x is a number ranging from 0.1 to 4;
y is a number ranging from 5 to 53;
p is a number ranging from 0 to 15;
obtained by means of a process which comprises putting the following components in contact:
(A) at least one zirconium arene having general formula (II):

$$Zr(\eta^6\text{-arene})_2Al_qX_r \qquad (II)$$

wherein:
arene represents a benzene, or a benzene substituted with from 1 to 6 linear or branched $C_1$-$C_6$ alkyl groups, or mixtures thereof;
X represents chlorine;
q is a number ranging from 2 to 6;
r is a number ranging from 8 to 20;
(B) tetrachlorides having general formula MCl$_4$ wherein M represents titanium; and, optionally,
(C) magnesium chloride (MgCl$_2$).

2. The solid catalyst component according to claim 1, wherein q is 3 in the case of zirconium arene having general formula (II).

3. The solid catalyst component according to claim 1, wherein r is 11 in the case of zirconium arene having general formula (II).

4. The solid catalyst component according to claim 1, wherein compounds (A), (B) and, optionally (C), are used in the following molar ratios (0.5-2):(1):(0-12), respectively.

5. The solid catalyst component according to claim 1, wherein in the zirconium arene having general formula (II), said arene is selected from: benzene, toluene, ortho-xylene, meta-xylene, para-xylene, 1,2,3-trimethylbenzene, 1,2,4-trimethylbenzene, 1,3,5-trimethylbenzene (mesitylene), hexamethylbenzene, or mixtures thereof.

6. The solid catalyst component according to claim 1, wherein said process comprises putting components (A), (B), and, optionally, (C), in contact with at least one organic chloro-derivative (D) which is selected from:
(a) di- or poly-chloroalkanes;
(b) alkyl esters of aliphatic carboxylic acids di- or tri-chloro-substituted on the carbon in alpha position with respect to the carboxyl; or (c) monochloro triphenylmethane or dichloro diphenylmethane carrying a carboxyalkyl group in para position of at least one of the phenyl rings.

7. The solid catalyst component according to claim 6, wherein the compounds (A), (B), and, optionally, (C) and (D) are used in the following molar ratios (0.5-2):(1):(0-12):(0-40), respectively.

8. The solid catalyst component according to claim 6, wherein said process comprises putting components (A), (B), and, optionally, (C) and (D), in contact with at least one aluminium alkyl chloride (E) which is selected from those having general formula:

$$Al(R_{13})_w Cl_{3-w}$$

wherein $R_{13}$ represents a linear or branched $C_1$-$C_{20}$ alkyl group; w is 1 or 2.

9. The solid catalyst component according to claim 8, wherein the compounds (A), (B), and, optionally, (C) and (D) and (E), are used in the following molar ratios (0.5-2):(1):(0-12):(0-40):(0-40), respectively.

10. The solid catalyst component of claim 1, wherein the zirconium arene has the formula:

$$Zr(\eta^6\text{-benzene})_2(Al_3Cl_{11}).$$

* * * * *